(12) United States Patent
Bissett, III et al.

(10) Patent No.: US 7,369,229 B2
(45) Date of Patent: May 6, 2008

(54) SPECTRAL IMAGING SYSTEM

(75) Inventors: William Paul Bissett, III, Tampa, FL (US); David D. R. Kohler, Tampa, FL (US); Robert G. Steward, St. Petersburg, FL (US); Curtis D. Mobley, Sammamish, WA (US)

(73) Assignee: Florida Environmental Research Institute, Inc., Tampa, FL (US)

( * ) Notice: Subject to any disclaimer, the term of this patent is extended or adjusted under 35 U.S.C. 154(b) by 356 days.

(21) Appl. No.: 10/996,530

(22) Filed: Nov. 24, 2004

(65) Prior Publication Data

US 2005/0151965 A1 Jul. 14, 2005

Related U.S. Application Data

(60) Provisional application No. 60/563,967, filed on Apr. 21, 2004, provisional application No. 60/545,803, filed on Feb. 19, 2004, provisional application No. 60/525,192, filed on Nov. 26, 2003.

(51) Int. Cl.
*G01J 3/28* (2006.01)

(52) U.S. Cl. ...................... 356/328; 356/305
(58) Field of Classification Search ........... 356/305, 356/326, 328
See application file for complete search history.

(56) References Cited

OTHER PUBLICATIONS

Kvitek, R.G. et al, "Early Implementation of Nearshore Ecosystem Database Project, Final Report" Jul. 27, 1999, pp. 43-48 XP002320986.

Mobley, C. et al. "A Look-Up Table Approach to Inverting Remotely Sensed Ocean Color Data" Ocean Optics XVI Conference, Nov. 22, 2002, Santa Fe, New Mexico, Abstract.

Morel, Andre, "Optical Modeling of the Upper Ocean in Relation to Its Biogenous Matter Content (Case I Waters)", J. of Geophysical Research, vol. 93, No. C9, pp. 10,749-10,768, Sep. 15, 1988.

Howard Gordon, et al., "A Semianalytic Radiance Model of Ocean Color," J. of Geophysical Research, vol. 93, No. D9, pp. 10,909-10,924, Sep. 20, 1988.

Chuanmin Hu et al., "Atmospheric Correction of SeaWiFS Imagery over Turbid Coastal Waters: A Practical Method," Remote Sens. Environ. 74:195-206 (2000).

David A. Siegel, et al., "Atmospheric correction of satellite ocean color imagery: the black pixel assumption,", Applied Optics, vol. 39, No. 21, pp. 3582-3591, Jul. 20, 2000.

Howard R. Gordon et al., "Clear water radiances for atmospheric correction of coastal zone color scanner Imagery", Applied Optics, vol. 20, No. 24, pp. 4175-4180, Dec. 15, 1981.

(Continued)

*Primary Examiner*—F. L. Evans
(74) *Attorney, Agent, or Firm*—Christopher Paradies; Fowler White Boggs Banker P.A.

(57) ABSTRACT

An imaging system and methods for resolving elements of interest through and obscuring environment by removing undesired signals from the intervening, obscuring environment is disclosed. A passive hyperspectral imaging sensor is calibrated and integrated into a system having a positioning and attitude detection system and an instrument control and data acquisition system that records data from sensors in a three-dimensional data cube having two spatial dimensions and a spectral dimension. Either an active detection and ranging system or a look-up-table approach or both are used to remove the noise generated by the intervening, obscuring environment from the data relevant to the elements of interest.

28 Claims, 21 Drawing Sheets

OTHER PUBLICATIONS

Ruddick, Kevin G., et al., "Atmospheric correction of SeaWiFS imagery for turbid coastal and inland waters", Applied Optics, vol. 39, No. 6, pp. 897-912, Feb. 20, 2000.

Kendall L. Carder, et al., AVIRIS Calibration and Application in Coastal Oceanic Environments, Remote Sens. Environ. 44:205-216 (1993).

Zhongping Lee et al., "Properties of the water column and bottom derived from Airbonre Visible Infrared Imaging Spectrometer (AVIRIS) data", J. of Geophysical Research, Vo. 106, No. C6, pp. 11639-11,651, Jun. 15, 2001.

Ronald J. Birk et al., "Airborne Hyperspectral Sensor Systems", IEEE AES Systems, pp. 26-33, Oct. 1994.

Eric M. Louchard, et al. "Optical remote sensing of benthic habitats and bathymetry in coastal environments at Lee Stocking Island, Bahamas: A comparative spectral classifcation approach", Limnol. Oceanogr. 48(1, part2), 2003, pp. 511-521.

Juanita C. Sandidge, et al. "Coastal Bathymetry Hyperspectral Observations of Water Radiance," Remote Sens. Environ 65:341-352 (1998).

Zhongping Lee et al., "Hyperspectral remote sensing for shallow waters: 2. Deriving bottom depths and water properties by optimization", Applied Optics, vol. 38, No. 18, pp. 3831-3843, Jun. 20, 1999.

Zhongping Lee et al., "Hyperspectral remote sensing for shallow waters: 1. A semianalytical model", Applied Optics, vol. 37, No. 27, pp. 6329-6338, Sep. 20, 1998.

Robert O. Green, "Spectral calibration requirement for Earth-looking imging spectrometers in the solar-reflected spectrum", Applied Optics, vol. 37, No. 4, pp. 683-690, Feb. 1, 1998.

Howard R. Gordon, et al. "Remote Assessment of Ocean Color for Interpretation of Satellite Visibile Imagery", Lecture Notes on Coastal and Estuarine Studies, pp. 72-83, 1983 (No Month).

"Google adds satellite maps" Tech News & Reviews- MSNBC.com, The Associated Press, Apr. 5, 2005 http://www.msnbc.msn.com/id/7394347.

David Kohler "An Evaluation of a Derivative Based Hyperspectral Bathymetric Algorithm", diss. Cornell Univ., May 2001.

Spectrum Mapping, LLC, Spectrum Mapping Exhibits LIDAR/Multi-Sensor Fusion and Feature Extraction, Nov. 6-10, 2006, Crowne Plaza Hotel, Riverwalk, San Antonio, Texas, Web page; http://www10.giscafe.com/nbc/articles/view_article.php?section=CorpNews.

Babey, S.K, et al., Radiometric Calibration of the Compact Airborne Spectrographic Imager (CASI), Canadian Journal of Remot Sensing, vol. 18, No. 4, Oct. 1992.

Harron, J.W., et al., "Methodologies and errors in the calibration of a compact airborne spectrographic imager", Candian Journal of Remot Sensing, Toronto, Jun. 1992.

Davis, et al., "Calibration, characterization and first results with Ocean PHILLS Hyperspectral . . . ", Part of the SPIE Conference on Imaging Spectrometry V, Denver, Jul. 1992, 1999.

Staenz, et al, "Processing/analysis capabilities for data acquired with hyperspectal spaceborne sensors", Acta Astronautica, vol. 39, No. 9-12, pp. 923-931, 1996.

Babey, S.K., "Development of a next-generation compact airborne . . . ", Fourth Int'l Airborne Remote Sensing Conference and Exhibition, Ottawa, Canada, Jun. 21-24, 1999.

Cosandier, et al., "Development of a Next Generation Compact Airborne Pushbroom . . . ", ISPRS Workshop, Integrated Sensor Orientation . . . , Barcelona, Spain, Sep. 4-8, 1995.

Cosandier, et al., "The integration of a digital elevation model in casi image . . . ", First Int'l Airborne Remote Sensing Conference . . . , Strasbourg, France Sep. 11-15, 1994.

Gibson et al, "A stereo electro-optical line imager for automated mapping", Int'l Symposium on Automated Cartography, Ottawa, Ontario, Oct. 16-21, 1983, pp. 165-176.

Gibson, "Processing stereo imagery from line imagers", Canadian Symposium on Remote Sensing, St. John's Nfld, Aug. 14-17, 1984, pp. 471-487.

Staenz, et al., "Retrieval of surface reflectance from hyperspectral data . . . ", Canadian Journal of Remote Sensing, vol. 23, No. 4, Dec. 1997.

Staenz, et al., "ISDAS-A system for Processing/Analyzing Hyperspectral Data . . . ", Canadian Journal of Remote Sensing, vol. 24, No. 2, Jun. 1998.

Fisher, et al., "Comparison of low-cost hyperspectal sensors", SPIE Conference on Imaging Spectrometry IV, San Diego, CA, Jul. 1998.

Davis, et al., "Calibration, Characterization and first results with ocean PHILLS hyperspectral imager", SPIE Conference on Imaging Spectrometry V, Denver, CO, Jul. 1999.

Lin, "ECOM Payload 721", http://ww.bu.edu/csp/uv/econ/payload.html, May 1998.

Gibson et al., "Geometric Correction of Airborne Linee Scanner Data", 11th Annual Canadian Symposium on Remote Sensing, University of Waterloo, Ontario, Jun. 22-25, 1987.

Gower, et al., "The fluorescence Line Imager: Imaging Spectroscopy . . . ", 11th Annual Canadian Symposium on Remote Sensing, University of Waterloo, Ontario, Jun. 22-25, 1987.

Anger et al., "Technological Enhancements to the Compact Airborne . . . ", First Int'l Airborne Remote Sensing Conference and Exhibition, Strasbourg, France, Sep. 11-15, 1994.

O'Hara, "Remote Sensing and Geospatial Applications for Wetland Mapping and Assessment", www.ncrste.msstate.edu/publicatins/ncrste_tg003.pdf, date?

Wetland Classifications using the Compact Airborne Spectrographic Imager (casis), Itres Research Limited, 2001.

Schenk, "Digital Photogrammetry", vol. 1, Terrascience, 1999.

Ivanco et al., "Casi Real-Time Surface-Laid Mine Detectino System", Itres Research LImited, Date(?).

Kohler, David, D.R., et al., "New approach for the radiometric calibration of spectal imaging systems", *Optics Express*, 2463, vol. 12, No. 11, May 31, 2004.

Mobley, Curtis D., et al., "Interpretation of hyperspectral remote-sensing imagery by spectrum matching and look-up tables", *Applied Optics*, vol. 44, No. 17, Jun. 10, 2005.

"Hyperspectral Plus LIDAR: Fusing Spectral Profiling & Terrain Modelling Capabilities", www.itres.com - Aug. 29, 2007.

SPECTRAL IMAGING SYSTEM

RELATED APPLICATIONS

This application claims the benefit of Provisional Application No. 60/525,192, filed Nov. 26, 2003; Provisional Application No. 60/545,803, filed Feb. 19, 2004 and Provisional Application No. 60/563,967, filed Apr. 21, 2004.

FIELD OF THE INVENTION

The spectral imaging system relates to systems for gathering information about features obscured by intervening environmental media.

BACKGROUND

Systems that use airborne platforms for imaging, such as satellites, aircraft and dirigibles, which are lighter than air at sea level, in order to remotely gather information are known. Passive spectral imaging of electromagnetic radiation, using natural sunlight as the illumination source, is capable of resolving information about elements of interest through a radiation obscuring media. Spectral imaging is a technology defined by the capturing and recording the electromagnetic radiation reflected and/or emitted from elements of interest. Conventional sensors focus on either the visible or infrared portions of the electromagnetic spectrum. The spectral response from the elements of interest, which are typically converted to electrical signals, such as by a charged coupled device (CCD), are discretized into numerous, narrow, contiguous wavebands. The number of wavebands used in multispectral imaging may vary from two relatively broad wavebands to many, narrower wavebands. By overlaying one waveband upon another, a three-dimensionally spectral data cube may be generated having spacial dimensions X and Y and a spectral dimension in the Z direction, for example.

Elements of interest are any features that the system is intended to detect by way of multispectral analysis. For example, bathymetry, temperature, salinity, natural and anthropogenic hydrocarbon spills and seepages, fresh water plumes, plankton blooms, pollutants, and tracking of fluorescent tracer dyes are examples of elements imaged by conventional spectral imaging. Spectral imaging may also be used for military applications to identify the location of elements of interest, including search and rescue, location of armaments and troops, detection of contaminants, observation of submerged or buried mines or other impediments, and tracking of supplies.

U.S. Pat. No. 6,008,492 ("the '492 patent") entitled "Hyperspectral Imaging Method and Apparatus" describes the state of the art at the time the '492 patent was filed. The '492 patent does not disclose the use of light or imaging or the use of any second order filters. Instead, the '492 patent teaches numerically correcting for second order of effects, disclosing the use of merely a 10 bit CCD system, which has an inadequate dynamic range for use in oceanographically obscured environmental media.

Light detection and ranging (LIDAR) uses spectrally narrow pulses of an electromagnetic frequency band that are emitted by a sensor. The return signals are measured using time-of-flight techniques, such as time gating and ranging, which are used to determine the distances and/or the velocity of light in the media through which the spectrally narrow pulses pass.

U.S. Pat. No. 5,450,125 ("the '125 patent") entitled "Spectrally Dispersive Imaging LIDAR System" discloses a LIDAR system that uses fluorescent decay properties and Raman emissions to collect spectral information. A cumulative, passive spectral response of the entire scene is returned to a narrow bandpass receiver. The spectral response is recorded without reserving the spatial information within the scene. Thus, the spectral response cannot be added as a layer of a multispectral image in a spectral data cube.

The complexity and variety of marine optical signals in coastal ocean areas has created a challenging environment for the development of remote sensing instrumentation and algorithms. To date, the most successful oceanic algorithms were based upon multispectral data streams and have been focused on the characterization of Case 1 type waters (waters where the optical constituents of the water co-vary with each other). See, H. R. Gordon and A. Morel, Remote assessment of ocean color for interpretation of satellite visible imagery, A review (Springer-Verlag, New York, 1983), p. 114; A. Morel, "Optical modeling of the upper ocean in relation to its biogenous matter content (Case I waters)," Journal of Geophysical Research 93(C9), 10, 749-710, 768 (1988); and H. R. Gordon, O. B. Brown, R. H. Evans, J. W. Brown, R. C. Smith, K. S. Baker, and D. K. Clark, "A semianalytic radiance model of ocean color," Journal of Geophysical Research 93(D9), 10, 909-910, 924 (1988). While these algorithms have worked well for classifying marine water types, they have been less successful in describing near shore environments. See, C. Hu, K. L. Carder, and F. E. Muller-Karger, "Atmospheric Correction of SeaWiFS Imagery over Turbid Coastal Waters: A Practical Method," Remote Sensing of Environment. Vol. 74, no. 2 (2000). The near shore environment has additional influences on the optical signals, which do not necessarily co-vary with signals produced by the ecology interactions. These additional signals include the influence of the bottom, which includes variations in the spectral signal and magnitude depending on the bathymetry and bottom type of the region. These bottom effects have temporal as well as spatial variations and include an impact due to seasonal changes in macrophyte coverage and re-suspended sediments. The algorithms are also hampered by colored degradation matter and sediments from terrestrial sources that contaminate the marine produced color signals.

The first step in any algorithm development for coastal optical remote sensing requires the accurate retrieval of water-leaving radiance, $L_W(\lambda)$, from sensor measured radiance. The sensor radiance signal is most often dominated by the atmospheric radiance additions and attenuations, such that $L_W(\lambda)$ is often just a small fraction of the measured photon density. The removal of the atmospheric interference in the water-leaving radiance signal requires a priori knowledge of a host of atmospheric constituents, e.g. water column water vapor, aerosol type and density, ozone concentration, etc. Without a priori knowledge, retrieval of these factors must be backed out from the spectral data stream itself, decreasing the degrees of freedom with which to resolve the water-leaving radiance signal. Additionally, the increased development along the world's coastal boundaries adds another layer of complexity for determining concentration and interactions between the marine and terrestrial aerosols. The atmospheric parameterization can change dramatically within a single scene in such a complex spectral environment.

Further complicating atmospheric correction in complex environment, such as a coastal marine environment, is the potential for bottom and suspended sediments. As opposed to deeper off shore waters, the assumption that these waters have no optical return in the near infra red is no longer valid. See, C. Hu, K. L. Carder, and F. E. Muller-Karger, "Atmospheric Correction of SeaWiFS Imagery over Turbid Coastal Waters: A Practical Method," Remote Sensing of Environment. Vol. 74, no. 2 (2000); See, D. Siegel, M. Wang, S. Maritorena, and W. Robinson, "Atmospheric correction of satellite ocean color imagery: the black pixel assumption," Applied Optics 39(21), 3582-3591 (2000); See, H. R. Gordon and D. K. Clark, "Clear water radiances for atmospheric correction of coastal zone color scanner imagery," Applied Optics 20(24), 4175-4180 (1981); and See, K. Ruddick, F. Ovidio, and M. Rijkeboer, "Atmospheric correction of Sea-WiFS imagery for turbid coastal and inland waters," Applied Optics 39(6), 897-912 (2000). These considerations coupled with the dominance of the atmosphere's optical effects over the weak optical return from the coastal environment make atmospheric correction of these coastal areas very difficult.

Promising to deliver the extra information needed to properly handle such spectrally complex scenes, hyperspectral remote sensing emerged as a collection tool more than a decade ago. See, R. J. Birk and T. B. McCord, "Airborne Hyperspectral Sensor Systems," IEEE AES Systems Magazine 9(10), 26-33 (1994) and See, K. L. Carder, P. Reinersman, R. F. Chen, F. Muller-Karger, C. O. Davis, and M. Hamilton, "AVIRIS calibration and application in coastal oceanic environments," Remote Sensing of Environment 44, 205-216 (1993). Hyperspectral remote sensing data, with its numerous, narrow, contiguous wavebands, approximate the true electromagnetic signature of its target. See, Z. Lee, K. L. Carder, R. F. Chen, and T. G. Peacock, "Properties of the water column and bottom derived from Airborne Visible Infrared Imaging Spectrometer (AVIRIS) data," Journal of Geophysical Research 106(C6), 11, 639-611, 652 (2001). With this new information, mathematical techniques originally developed in laboratory spectroscopy were applied to this data set in an attempt to characterize the imagery. There have been some recent efforts to use high spectral data in the mapping of the coastal zone. See, D. D. R. Kohler, "An evaluation of a derivative based hyperspectral bathymetric algorithm," Dissertation Cornell University, Ithaca, N.Y., (2001); See, E. Louchard, R. Reid, F. Stephens, C. Davis, R. Leathers, and T. Downes, "Optical remote sensing of benthic habitats and bathymetry in coastal environments at Lee Stocking Island, Bahamas: A comparative spectral classification approach," Limnol. Oceanogr. 48(1, part 2), 511-521 (2003); See, J. C. Sandidge and R. J. Holyer, "Coastal bathymetry from hyperspectral observations of water radiance," Remote Sensing of Environment 65(3), 341-352 (1998); See, Z. Lee, K. L. Carder, C. D. Mobley, R. G. Steward, and J. S. Patch, "Hyperspectral remote sensing for shallow waters: 2. Deriving bottom depths and water properties by optimization," Applied Optics 38(18), 3831-3843 (1999); and See, Z. Lee, K. L. Carder, C. D. Mobley, R. G. Steward, and J. S. Patch, "Hyperspectral remote sensing for shallow waters. 1. A semianalytical model," Applied Optics vol. 37(no. 27), 6329-6338 (1998). However, the sensors used to collect the data for these previous studies suffer from sensitivity and calibration issues that become apparent in these low light scenes. The instruments' limitations require an on-site, vicarious calibration of the data to be useful in these environments. See, K. L. Carder, P. Reinersman, R. F. Chen, F. Muller-Karger, C. O. Davis, and M. Hamilton, "AVIRIS calibration and application in coastal oceanic environments," Remote Sensing of Environment 44, 205-216 (1993). This in turn, reduces the applicability of these tools and techniques to other coastal areas, or even other water-types within the same image. In addition, remote sensing data analyses, such as temporal scene-to-scene comparisons, are virtually impossible to interpret if the physical units of the individual images are in question. This demand for a high degree of radiometric certainty has to date inhibited this data stream from reaching its full potential as an oceanographic tool. Therefore for newly developed algorithms to be of greater use, there is a long standing and unresolved need for hyperspectral data having a high confidence in absolute radiometric calibration. See, R. O. Green, "Spectral calibration requirement for Earth-looking imaging spectrometers in the solar-reflected spectrum," Applied Optics 37(4)., 683-690 (1998).

SUMMARY OF THE INVENTION

A system for remotely sensing coastal marine environments is useful for imaging many different environments that require information to be gathered from images obscured by intervening environmental media. The system comprises a calibrated spectral imaging sensor. The method for calibrating the spectral imaging sensor may use filters to extend the radiometric calibration range and a calculation that accounts for the filter effect on all viewing angles of the spectral imaging sensor. In one embodiment, a radiometric calibration map is derived, using data collected using filters, that is applied to the signals from the passive spectral imaging sensor by the imaging system. For example, a correction may be included in the map for the residual stray light and frame transfer smear in any data stream produced by the passive spectral imaging sensor, such that the passive spectral imaging sensor accurately detects the frequencies of light for elements of interest from a variety of different obscuring media, such as a marine environment.

In one embodiment, the system comprises a electromagnetic radiation detecting and ranging system, such as a light detecting and ranging (LIDAR) system, and method for coupling multispectral imaging and LIDAR data as remotely sensed data, a method of storing and retrieving the remotely sensed data and a method for processing remotely sensed data, in order to correct for an intervening environmental media that obscures the elements of interest.

Alternatively, or in addition, the data acquisition and storing system uses a look-up-table (LUT) approach to correct for the most-comparable, intervening environment media that is contained in a LUT database.

Passive spectral imaging of the electromagnetic radiation from the target and media uses a continuous broad wavelength of electromagnetic radiation such as natural sunlight to illuminate the elements of interest and the environment. Spectral imaging defines a technology whereby the individual electromagnetic responses of elements found within a scene are captured and recorded. Spectral imaging incorporates any spectroscopy technique employing multiple wavelengths. The active imaging of LIDAR (Light Detection And Ranging) uses spectrally narrow pulses of electromagnetic radiation which are emitted by the sensor and the return signal is measured with time-of-flight techniques such as time gating and ranging. This allows retrieval of target characterization and classification from any fluid or obscured medium by combining information regarding both the spectral signature of the elements of interest and the location of the elements of interest within the fluid medium.

One system comprises a spectral imager coupled with an imaging LIDAR on a single moving platform Another system comprises a spectral imager coupled with an imaging LIDAR on either a single stable platform or on multiple platforms. In one embodiment, a system comprises a spectral imager coupled with an imaging LIDAR and a topographic LIDAR. Still another system comprises a spectral imager with an imaging LIDAR and a topographic LIDAR on a single stable platform Another system comprises a spectral imager coupled with an imaging LIDAR and a bathymetric LIDAR. Still another system comprises a spectral imager coupled with an imaging LIDAR and a bathymetric LIDAR on a single stable platform.

Extraction of environmental information, such as water inherent optical properties (IOPs) and shallow-water bottom depth ($z_b$) and spectral reflectance ($R_b$) from remotely-sensed hyperspectral ocean-color data, uses a look-up-table (LUT) approach, in one example that compares a measured remote-sensing reflectance ($R_{rs}$) spectrum with tabulated $R_{rs}$ spectra generated by a large number of numerical radiative transfer modeling runs. The runs use a wider range of water IOPs, bottom depths and reflectances, solar angles and viewing directions. The environmental conditions corresponding to the measured $R_{rs}$ spectrum are presumed to be the same as the input conditions for the radiative transfer modeling run that generated the database $R_{rs}$ spectrum. LUT method works very well. Non-uniqueness of $R_{rs}$ spectra does not appear to be a problem, and wavelength-uncorrelated random noise does not affect the spectrum matching.

BRIEF DESCRIPTION OF THE DRAWINGS

The drawings show examples of the present invention, which is not limited to the specific examples as represented in the drawings.

DETAILED DESCRIPTION OF PREFERRED EMBODIMENTS OF THE INVENTION

This detailed description and the drawings provides specific examples of the invention, but the invention should not be limited merely to the examples disclosed. Instead, the invention should be limited only by the claims that may eventually issue. Many variations in the system, changes in specific components of the system and uses of the system will be readily apparent to those familiar with the area of remote sensing based on the drawings and description provided.

Figure 1:
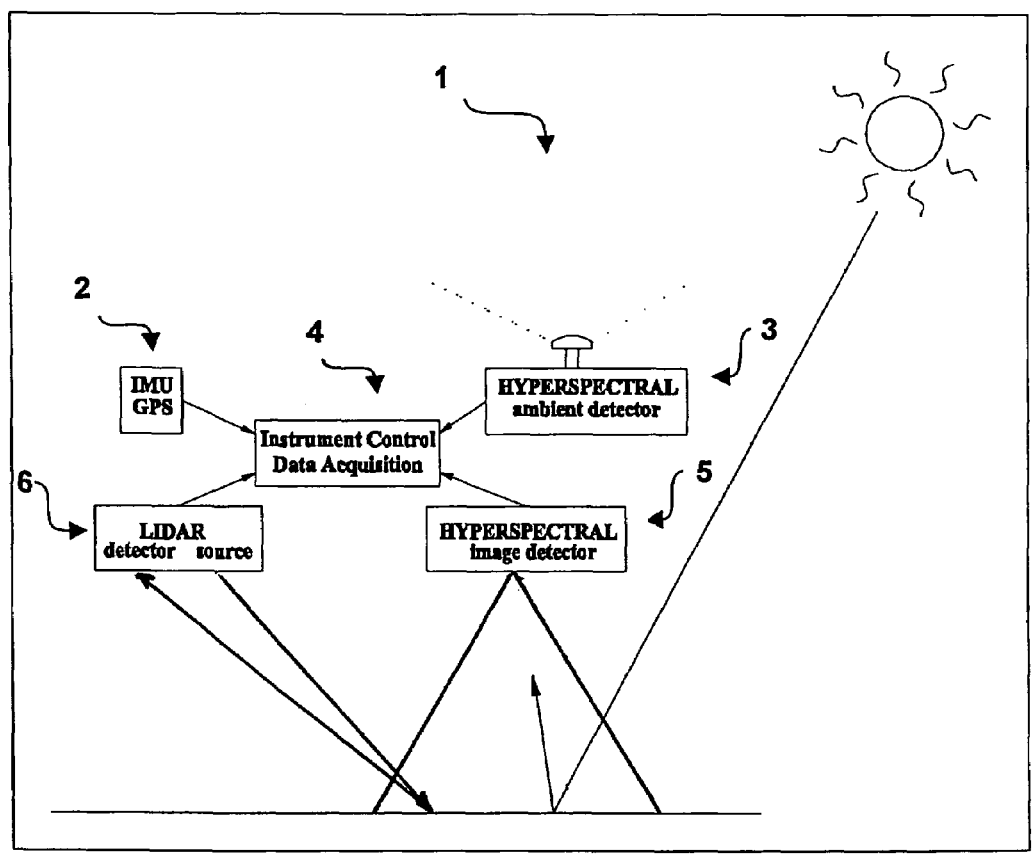
FIG. 1 depicts an embodiment of the combined sensor system.

In one embodiment, a system of remotely sensing coastal marine environments is developed that has the capability of coupling a multispectral imaging sensor and a LIDAR system to improve the resulting information obtained on elements of interest within the coastal marine environment, such as shown in FIG. 1.

One embodiment includes a device and method for calibrating a spectral imaging camera. The system may also include a method for processing remotely sensed, multi-spectral data, such as the capability of determining from the remotely sensed hyperspectral ocean color data, itself, the inherent optical properties, shallow-water bottom depth, and spectral reflectance, such as by using a look-up-table (LUT) approach. Using these values, image analysis may be performed, such as real-time image analysis, to filter from the signals at least a portion of the signal caused by the intervening, obscuring environment, which then better reveals the elements of interest.

The system is capable of recording and retrieving the remotely sensed data of both the multispectral imaging and the LIDAR system efficiently, such that storage requirements are reduced without loss of information, such as by storing information in an imaging data cube. For example, the multispectral imaging camera and LIDAR system may be mounted on a single airborne platform. In an alternative example, multiple platforms are used and the data is spatially resolved to provide a three-dimensional spectral data cube. For example, position information may be recorded during flight by a positioning system, such as a global positioning satellite system and gyroscopic data for angles, or any other positioning system providing accurate positioning information.

The imaging sensor may be prepared to provide a high confidence in its absolute radiometric calibration. A technique that uses filters to extend the radiometric calibration range is combined with a calculation for the filter effect that accounts for all viewing angles of the system Using the data collected with the filters in place, a correction for the residual stray light and frame transfer smear inherent in a data stream produced by an imaging sensor, such as the PHILLS 2 sensor, is derived. While this calibration system was developed for the PHILLS 2 sensor, it is universal in nature and can be applied to other spectral imaging systems to assess and correct similar problems, providing a high confidence in the system's absolute radiometric calibration.

In one embodiment, a new approach for the radiometric calibration of spectral imaging systems is used. The calibration of multispectral and hyperspectral imaging systems uses an integrating sphere, which usually produces a signal that is red rich. Using such a source to calibrate environmental monitoring systems presents some difficulties. Not only is much of the calibration data outside the range and spectral quality of data values that are expected to be captured in the field, but also using these measurements alone may exaggerate the optical flaws found within the system. Left unaccounted for, flaws are embedded into the calibration, and are passed on to the field data when the calibration is applied. In one embodiment, a series of well characterized spectral filters are used within the calibration process to improve the calibration.

For example, a Portable Hyperspectral Imager for Low-Light Spectroscopy 2 (PHILLS 2) is an aircraft mounted, push broom type hyperspectral imaging sensor. It utilizes a two dimensional charge coupled device (CCD) camera to collect the spectral information along a single line on the ground, such as perpendicular to the direction the aircraft is traveling. As the aircraft moves forward along its trajectory, the sensor's CCD camera captures the spatially dependent spectral information one frame at a time across a thin swath of ground, and thus, as each along-track frame is assembled an image cube is built. The integration time of the sensor is a function of the frame rate of the camera. The spatial resolution in the cross-track direction is dependent upon the sensor's lens, CCD dimensions, and aircraft altitude. While the along-track spatial resolution is also a function of the lens and altitude, it is more dependent on the frame rate of the camera and speed of the aircraft than is the cross-track spatial resolution. See, C. O. Davis, J. Bowles, R. A. Leathers, D. Korwan, T. V. Downes, W. A. Snyder, W. J. Rhea, W. Chen, J. Fisher, W. P. Bissett, and R. A. Reisse, "The Ocean PHILLS Hyperspectral Imager: Design, Characterization, and Calibration, "Optics Express 10(4), 210-221 (2002) provides a detailed description of the PHILLS sensor, which is incorporated herein, as background, in its entirety.

In one embodiment, the sensor was designed specifically for oceanic and near-shore hyperspectral remote sensing. Capturing coastal optical signals from an airborne platform poses two major design challenges that are not usually considered for terrestrial focused systems.

The first challenge for coastal environments is signal sensitivity. Imaging over optically deep waters and at high altitudes, the atmosphere makes up the majority of the observed signal (–0.90-100%). See, A. Morel, "In-water and remote measurement of ocean color," Boundary-Layer Meteorology 18, 117-201 (1980). This combined with the non linear attenuation properties of water requires a sensor have a high degree of sensitivity in order to properly map the water's subtle spectral characteristics. In the coastal environment, this is compounded by the relatively bright returns from shallow areas in which the effect of the bottom albedo is visible. The challenge is to resolve both shallow and deep water signals effectively without saturating the sensor's CCD while also imaging adjacent bright land or clouds. Limited dynamic range sensors need to compromise between the range of signals they can detect and the degree of sensitivity they can detect those signals. To overcome this limitation, one embodiment of the invention utilizes a high dynamic range camera such as 14 bit PlutoCCD camera from PixelVision, to capture the spectral information.

The second challenge for coastal environments is the spectral characteristics of the target, itself. Water is a blue dominant target. However, traditional charged coupled device (CCD) cameras are inherently inefficient in detecting blue light. This limitation was accounted for by the employment of a Scientific Imaging Technologies' (SITe) thinned, backside-illuminated CCD. Thinned, backside illuminated chips are essentially normal CCD chips except the silicon wafer that the chip was constructed from was thinned and the chip is flipped upside down when it is mounted in the camera. This process lets incident photons avoid encountering the silicon nitride passivation layer and silicon dioxide and polysilicon gate structures on the front side of the chip before being recorded by the silicon substrate. See, C. M. Huang, B. E. Burke, B. B. Kosicki, R. W. Mountain, P. J. Daniels, D. C. Harrison, G. A. Lincoln, N. Usiak, M. A. Kaplan, and A. R. Forte. "A new process for thinned, back-illuminated CCD imager devices," presented at the International Symposium on VLSI Technology, New York, (1989); and See G. M. Williams, H. H. Marsh, and M. Hinds, "Back-illuminated CCD imagers for high information content digital photography," presented apt the Digital Solid State Cameras: Designs and Applications, San Jose, Calif., (1998). This greatly increases the quantum efficiency of the chip from 5% to 60% at 400 nm and from –40% to 85% at 700 nm. See, G. M. Williams, H. H. Marsh, and M. Hinds, "Back-illuminated CCD imagers for high information content digital photography," presented apt the Digital Solid State Cameras: Designs and Applications, San Jose, Calif., (1998); and See, Scientific Imaging Technologies., Inc., "The CCD Imaging Array: An Introduction to Scientific Imaging Charge-Coupled Devices," Beaverton, Oreg., (1994). Although the quantum efficiency of the chip is greatly increased, this procedure does have its disadvantages. By avoiding the silicon gate structures, the probability of blooming occurring during CCD saturation conditions is greatly increased. Blooming happens when a single CCD well over flows due to saturation and its overflow corrupts its neighboring cells. The SITe CCD chip that the imaging sensor of this embodiment employs is broken up in to four quadrants, each with its own analog to digital converter. This division allows the chip to clock off data at a faster rate. The ability of this camera to achieve very fast frame rates allows for the flexibility in selecting a frame rate (1/integration time) in which the maximum brightness of the expected target does not approach saturation; therefore, the probability of CCD blooming is diminished.

Faster frame rates equate to shorter integration times; therefore, a sensor having a high quantum efficiency is selected, such that the sensor's chip offsets the short integration time over dark marine environments. To further improve blue light throughput, a spectrograph for hyperspectral imaging is selected that is optimized to be efficient at shorter wavelengths, such as the American Holographics (now Agilent Technologies) HyperSpec VS-15 Offier Spectrograph See, C. O. Davis, J. Bowles, R. A. Leathers, D. Korwan, T. V. Downes, W. A. Snyder, W. J. Rhea, W. Chen, J. Fisher, W. P. Bissett, and R. A. Reisse, "The Ocean PHILLS Hyperspectral Imager: Design, Characterization, and Calibration," Optics Express 10(4), 210-221 (2002). Also, the camera data is spectrally binned to enhance the signal to noise ratio. For example, the PHILLS 2 utilizes a 652 by 494 (spatial by spectral dimension) CCD. The spectral resolution is ~1.1 nanometer prior to binning and ~4.4 nanometers after binning.

The calibration of the sensor is a multi-step process that includes spectral calibration, angular response characterization, and radiometric calibration.

Spectral Calibration

As light enters a hyperspectral sensor, it passes through a spectrograph prior to being recorded by the CCD camera. The spectrograph separates the incoming light into its wavelength components. The spectral calibration is a determination of the relationship between the true spectral position of the incoming light and the observed effect.

In order to determine this relationship, a spectral element lamp is set up in front of the sensor. Between the lamp and the sensor, a piece of ground glass is placed to diffuse the source insuring that the entire aperture of the detector is illuminated. Sensor data is then collected using krypton, oxygen, hydrogen, helium, mercury and argon lamps. The combination of these lamps is selected to produce emission lines that together cover the full spectral range of the PHILLS 2 sensor (e.g., ~400 to 960 nanometers). The known spectral wavelengths of the emission lines are then regressed against the position of the pixels within the sensor in which the response was recorded.

Figure 3:
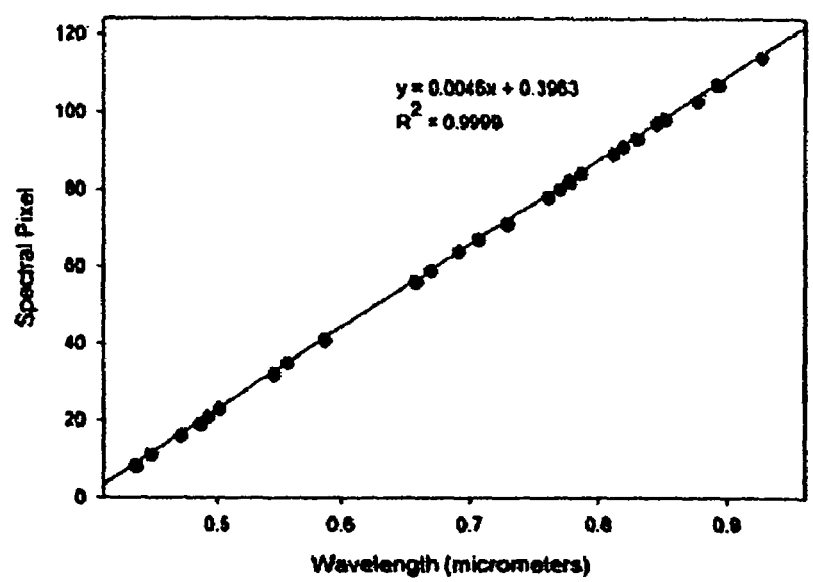
FIG. 3 shows a graph of a first order regression of the spectral position of element lamps and observed PHILLS 2 spectral pixel for spatial position 300.

The optical design and construction of the sensor PHILLS 2 is selected such that the CCD plane is perpendicular to the incoming diffracted light. A first order regression properly characterizes the spectral calibration data, as shown in FIG. 3. A demonstrated need for a higher order regression shows that the camera is misaligned in its relationship to the spectrograph, or that the CCD and/or the spectrograph failed to meet specifications or has been damaged.

Figure 2:
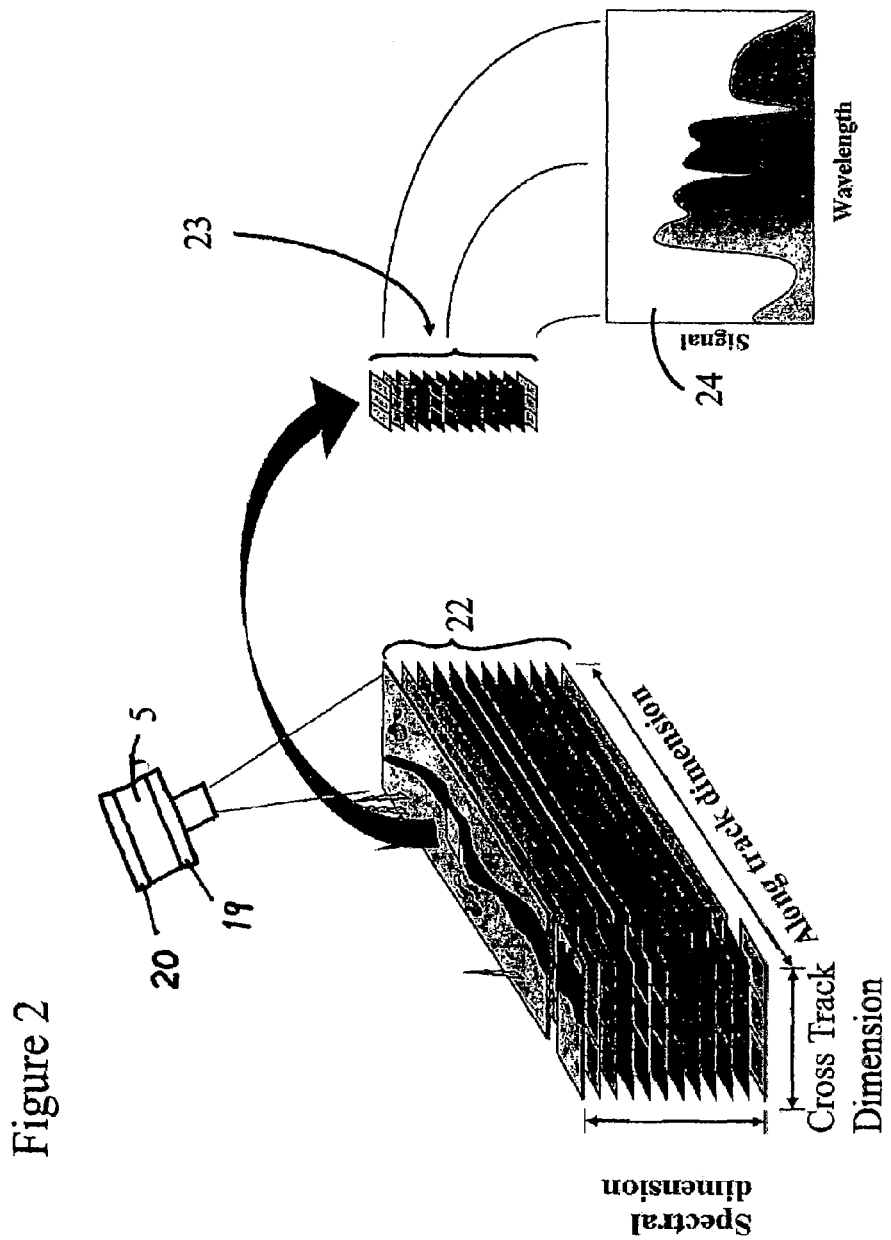
FIG. 2 shows the along-track and cross-track orientation of a pushbroom type sensor 20 on a satellite and the relationship to a three-dimensional data cube.

The regression of FIG. 3 is performed for every spatial element of the CCD. How this regression performs as a function of spatial position illustrates the spectral smile of the sensor. Smile is a function of all diffraction gratings; however, the sensor is specifically designed to have minimal smile effects. See, C. O. Davis, J. Bowles, R. A. Leathers, D. Korwan, T. V. Downes, W. A. Snyder, W. J. Rhea, W. Chen, J. Fisher, W. P. Bissett, and R. A. Reisse, "The Ocean PHILLS Hyperspectral Imager: Design, Characterization, and Calibration," Optics Express 10(4), 210-221 (2002). As can be derived from FIG. 2, the sensor is perpendicular to the projection of the spectrograph. The rotation of the camera within this perpendicular plane cannot be determined. Any rotational tilt would be convolved into the projection of the sensor's smile. As shown by FIG. 2, the smile-tilt of the sensor is small (−1.15 tun over 652 spatial pixels).

The sensor's smile-tilt is described on a sub-pixel scale. In developing the spectral calibration, the element lamp data is fit with a series of Gaussian curves. The relatively coarse spectral scale (binned to ~4 nm) of the sensor used in this example is not fine enough to detect the true position of the spectral peaks. The peaks that make up the observed spectral elements response are each modeled with a Gaussian curve. The position of the peak of this fit is then equated to a true spectral position of the element peak within the CCD. These derived positions are then propagated through the remainder of the spectral calibration. Once the smile-tilt relationship is determined for all the recorded spectral lamp responses across the spatial dimension of the CCD, a smile-tilt map of the CCD can be generated, as illustrated by FIG. 3. This smile-tilt map is then used to warp all future data (both lab calibration and field data) to a set wavelength vector.

Angular Response Characterization

An angular response characterization is a procedure developed to determine the viewing angle of every pixel within the spatial dimension of the sensor. A physically thin, spectral light source is set up a fixed distance away from the sensor. The distance of the source is selected such that its response within the sensor occupies only one spatial pixel in width. Once this distance is determined, the source is maintained in a plane parallel to the focal plane of the sensor. Next, the position along this plane that is both perpendicular to this plane and inline with the center of the sensor's focal plane is determined, and the source is then positioned there. The source is then repositioned along the parallel plane at predetermined intervals and the corresponding positions of the responses within the CCD are recorded. Employing the physical geometry of the sensor and the source through out the trials, the angular displacements of the source are derived. These measurements are then regressed against the observed CCD spatial position, which in turn produces a map of the angular response of the sensor.

Figure 4:
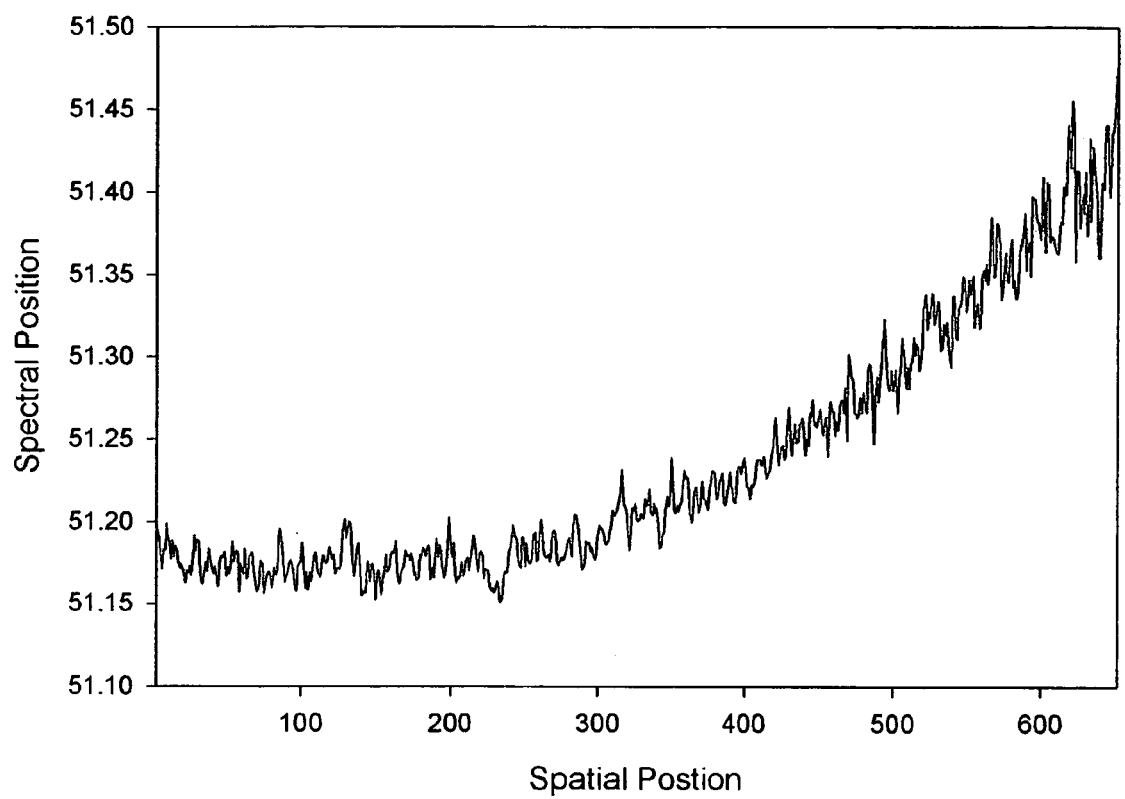
FIG. 4 shows a graph of the observed PHILLS 2 spectral position of a 0.6328 micrometer laser across the full spatial range of the CCD. One spectral position is approximately 4.6 nanometers.

As illustrated in FIG. 4, the sensor's angular response is nearly symmetrical. Also, the angular spacing is linear. This shows that the spectrograph-sensor alignment is adequate for use as a hyperspectral sensor. The sensor's keystone, the spatial equivalent of spectral smile, may be determined using this procedure. However, a spectral source should be selected that extends into the near infrared, if this is to be accomplished. A sensor should be selected that has a substantially negligible keystone. The spatially dependent angular response as a function of spectral position shown in FIG. 4 for visible light indicates that the sensor has substantially no keystone.

Radiometric Calibration

Figure 5:
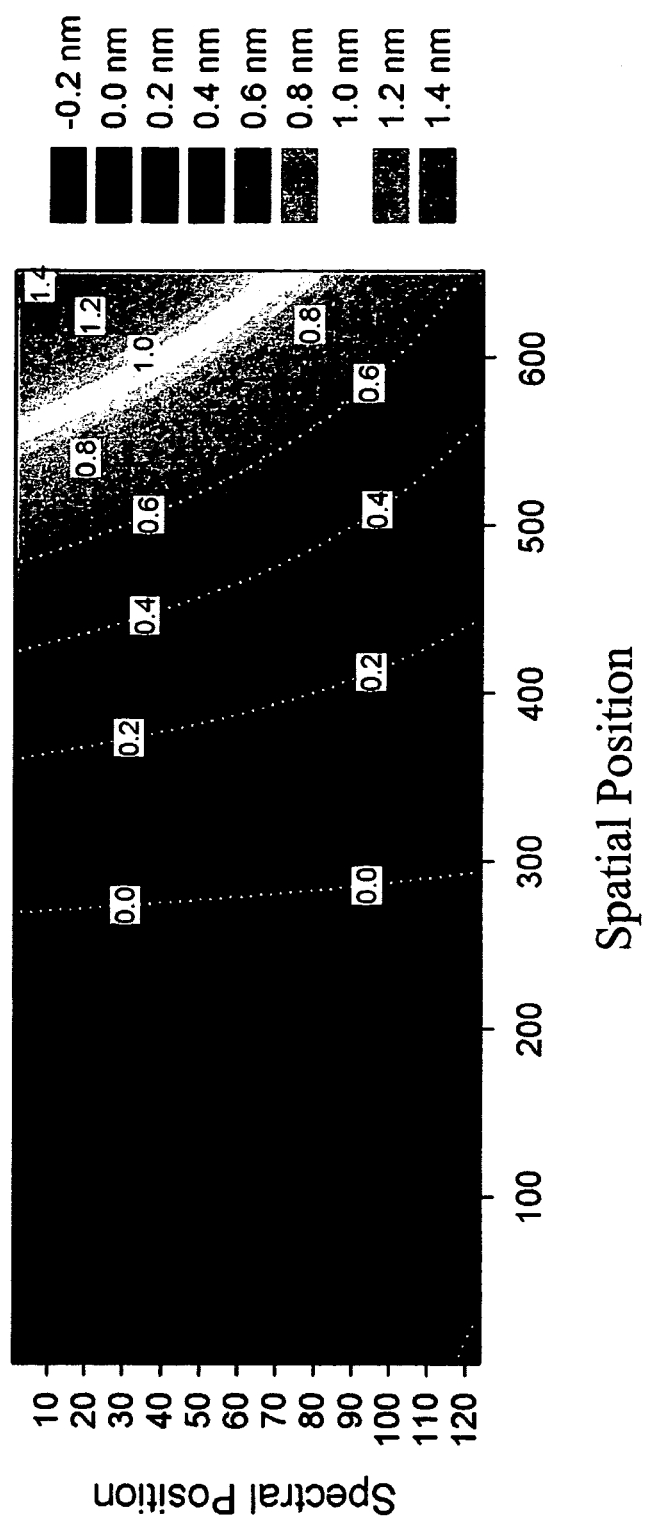
FIG. 5 shows a graph of a spectral smile map of the CCD illustrating the difference in nanometers between the spectral regression per spatial position and spectral regression at spatial position 280.

Simply stated, radiometric calibration relates the digital counts recorded by the sensor to the true physical units of the signal being sampled. Silicon CCD's are generally considered linear sensors with respect to intensity. See, G. M. Williams, H. H. Marsh, and M. Hinds, "Back-illuminated CCD imagers for high information content digital photography," presented apt the Digital Solid State Cameras: Designs and Applications, San Jose, Calif., (1998). A method is sued to verify this relationship by testing the sensor with a ten lamp, 40-inch diameter, Labsphere integrating sphere as our known source. The lamps and sphere may be calibrated to NIST-traceable standards (National Institute of Standards and Technology) prior to the taking of our measurements (e.g., within one month). The tungsten-halogen lamps that are utilized within the integrating sphere are red rich. This is not ideal for oceanic signals, which are blue rich. As shown in FIG. 5, using the sphere measurements without filters is not sufficient. Most of the ocean target spectra are outside of the calibration range of the sphere, resulting in the extrapolation of the retrieved upwelling radiance values from regions outside of the calibration series. With this extrapolation left unaccounted, the effects of small flaws and imperfections within the spectrograph and camera are exaggerated. These exaggerated values become imbedded within the radiometric calibration; therefore, errors will propagate to the field data when the calibration is applied. A series of filters is employed to correct the spectra such that the calibration spectra more closely resemble the expected field spectra. The use of these filters over a range of lamp intensities allows us to provide a calibration series that covers substantially the entire spectral range of expected targets. See, C. Cattrall, K. L. Carder, K. J. Thome, and H. R. Gordon, "Solar-reflectance-based calibration of spectral radiometers," Geophysical Research Letters 29(20), 2.1-2.4 (2002); and See, P. N. Slater, S. Biggar, J. M. Palmer, and K. J. Thome, "Unified approach to absolute radiometric calibration in the solar reflective range," Remote Sensing of Environment 77, 293-303 (2001).

A push broom type sensor has different pixels in the cross track viewing the targets at different angles. Any additional pathlength through the filter for off-angle measurements is accounted for prior to utilizing the filter measurements within the calibration. An estimation of the effective filter transmission can be derived for every viewing angle using angular response measurements, as detailed previously.

A filter should be selected having uniform thickness such as a Schott color glass filter having specifications that the front and back planes are parallel to within two arc minutes.

Care is taken when placing the filter in the filter holder prior to the collection of the calibration measurements to ensure that the filter is placed parallel to the plane of the sensor's aperture. For examples, a filter holder may be integrated in to the sensor's design. An integrated holder allows for consistent measurements from one calibration to the next. Also, since the filter holder is a permanent part of the sensor, its effect on the calibration measurements does not need to be considered prior to applying the calibration set to field data. In one embodiment, the filter holder reduces the impact of off angle environmental stray light by functioning similar to a photographic lens hood on traditional imaging system If the filter holder was not integrated in to the sensor design, its effect on the calibration data stream should be accounted for prior to completing the calibration processing.

Prior to the calibration, the total transmission of each of the filters is measured at a zero off angle, using a spectrophotometer, such as a Perkin Elmer Lambda 18 UVNIS Spectrophotometer. The influence that the front plane, back plane, and internal medium had on the total transmission was not measured, and transmission at wider angles, where the influence of the internal medium is a greater percentage of the total transmission might lead to small errors. Filters should be selected that reduce off angle errors.

The total filter transmission is summarized by the following equation:

$$T_t = t_i(1-r)(1-r').$$

where: $T_t$ is the total filter transmission, $t_i$ is the transmittance of the filter media, r is the reflectance due to the front side of the filter (air-filter interface), and r' is the reflectance due to the back side of the filter (filter-air interface). All four parameters are a function of wavelength and angle. In order to determine the losses due to the front and back plane reflectance, Snell's Law was employed to figure out the path angle within the filter for a particular viewing angle. See, A. Ryer, Light Measurement Handbook (International Light, Inc., Newburyport, Mass., 1997), p. 64:

$$\theta_{filter,\lambda} = \sin^{-1}\left[\frac{n_{air}\sin(\theta_{air})}{n_{filter,\lambda}}\right]$$

where: n is the index of refraction and $\Theta$ is the corresponding angle. The index of the refraction for the filter was supplied by the manufacturer. In the previous section, we measured the angular resolution of every spatial pixel of the sensor. With this angular information the reflectance losses may be determined via Fresnel's formula. See, A. Ryer, Light Measurement Handbook (International Light, Inc., Newburyport, Mass., 1997), p. 64. and See, C. D. Mobley, Light and Water (Academic Press, San Diego, Calif., 1994), p. 592:

$$r_{\theta=N,\lambda} = \frac{1}{2}\left[\left(\frac{\sin(\theta_{air}-\theta_{filter,\lambda})}{\sin(\theta_{air}+\theta_{filter,\lambda})}\right)^2 + \left(\frac{\tan(\theta_{air}-\theta_{filter,\lambda})}{\tan(\theta_{air}+\theta_{filter,\lambda})}\right)^2\right]$$

and $$r'_{\theta=N,\lambda} = \frac{1}{2}\left[\left(\frac{\sin(\theta_{filter,\lambda}-\theta_{air})}{\sin(\theta_{filter,\lambda}+\theta_{air})}\right)^2 + \left(\frac{\tan(\theta_{filter,\lambda}-\theta_{air})}{\tan(\theta_{filter,\lambda}+\theta_{air})}\right)^2\right]$$

These expressions are valid if $\Theta_{air}$ is not equal to zero (if $\Theta_{filter,\lambda}$ equals zero $\Theta_{air}$ must also equal zero according to equation (2)). In this case that $\Theta_{air}$ equals zero, the surface reflectance is equal to:

$$r_{\theta=0,\lambda} = r'_{\theta=0,\lambda} = \left[\frac{n_{filter,\lambda}-1}{n_{filter,\lambda}+1}\right]^{-2}$$

The determination of the effective internal transmission utilizes the Bouger's Law (or Beer Lambert) See, A. Ryer, Light Measurement Handbook (International Light, Inc., Newburyport, Mass., 1997), p. 64, which states:

$$\frac{\log_{10}(t_{i,\theta=0,\lambda})}{\log_{10}(t_{i,\theta=N,\lambda})} = \frac{d_{\theta=0,\lambda}}{d_{\theta=N,\lambda}}$$

where: $d_{\Theta=0,\lambda}$ and $D_{\Theta=N,\lambda}$ are the distances through the filter at the zero and N angle respectively. Using Snell's Law (equation (2)) and geometry, the ratio of the distances can be found via:

$$\frac{d_{\theta=0,\lambda}}{d_{\theta=N,\lambda}} = \cos\left[\sin^{-1}\left(\frac{\sin(\theta_{air})n_{air}}{n_{filter,\lambda}}\right)\right]$$

By combining equations (3) through (6), the total transmission at an off angle of N can be solved by:

$$T_{\theta=N,\lambda} = 10 \wedge \left[ \frac{T_{\theta=0,\lambda}}{(1-r_{\theta=0,\lambda})(1-r_{\theta=N,\lambda}^1)} \frac{d_{\theta=N,\lambda}}{d_{\theta=0,\lambda}} \right] (1-r_{\theta=N,\lambda})(1-r'_{\theta=N,\lambda})$$

Utilizing Equation (7), a filter map that corresponds to the view angles of the sensor's CCD is generated for each filter. Using these effective filter transmission maps, the filters are employed such that the range and spectral shape of the sphere data more closely resembles optical signals to be detected from elements of interest, as illustrated in FIG. 5.

Figure 8A:
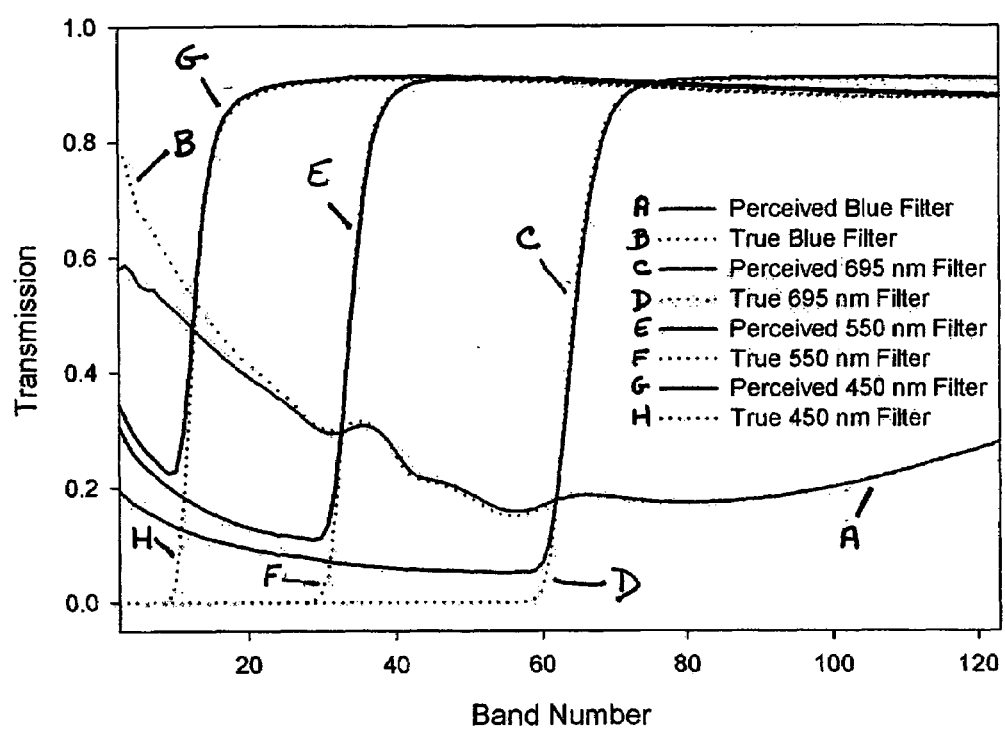
FIGS. 8(a-c) illustrates the PHILLS 2 derived filter transmission compared to independent filter transmission measurement for spatial pixel 280: prior to placement of zero order mask (8a), after placement of zero order mask (8b), and after stray light-frame transfer smear was addressed (8c). Only three of the six filters employed in the study are displayed.

The mismatch of the calibration lamp spectra and the anticipated spectra of the elements of interest might result in incorrect calibration of the final data stream. Spectral stray light and other artifacts inherent to the sensor are exaggerated by incorrect calibration, which carries the errors onto radiometric calibration. To characterize the instrument's combined spectral and radiometric response, a set of measurements is taken in front of a sphere through several different filters (three long-pass cutoff filters and three blue balancing filters). Utilizing these measurements and a measurement of the sphere without the filters present, a sensor perceived filter transmission is determined.

$$PT_\lambda = \frac{dn_{filtered,\lambda}}{dn_{unfiltered,\lambda}}$$

where: $PT_\lambda$ is the sensor's perceived filter transmission and $dn_\lambda$, is the raw, dark current corrected, digital number recorded by the sensor. Using Equation (8), the perceived filter transmissions are determined as illustrated in FIG. 8a). As shown in FIG. 8a the perceived filter does not approach the true filter transmission in the blue part of the spectrum.

Figure 8B:
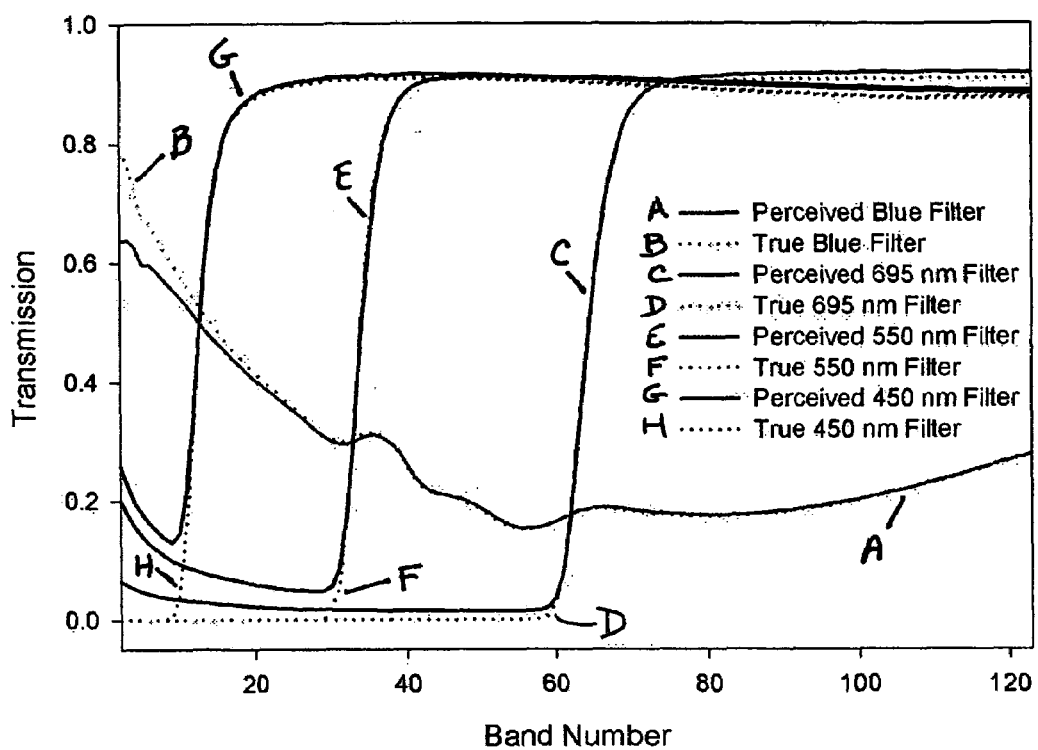

A light trap is placed within the sensor to shield the CCD from undiffracted light (zero order effect). The data was resampled with the shielded sensor, and the perceived filters were then recalculated, as illustrated in FIG. 8b. The sensor design limits the influx of UV light, and second order light greater than 515 nm is also blocked by a filter. The combination of these filters and the light trap reduces any errors from zero and first order diffracted light. While there is marked improvement after the placement of the light trap, the perceived filter responses still shows errors are present.

Two sources of error are that remain are out-of-band responses and frame transfer smear. Out-of-band response occurs when some percentage of photons are recorded on the sensor's CCD outside of their intended spectral position due to imperfections in the diffraction grating. All diffraction grating spectrometers exhibit this error. Frame transfer smear occurs in a shutterless system, such as the PHILLS 2. During the transfer of individual frames off the CCD, the CCD is left open to collect more data. The CCD transfers information in a circular "bucket-brigade" fashion. A single chain of CCD wells in the spectral dimension is a continuous bucket-brigade. As one spectral pixel's information is delivered and discharged, the bucket is moved back to the end of the array and the remaining CCD values shift one well (bucket) closer to the read out row. This process continues until the entire spectral dimension is read off and each of the buckets are back in there original position, ready for another integration period. During advancement back to their original position and during their wait to be read off, the remaining CCD values are acquiring additional information. This additional information is not inherently their own. Instead, the information was intended for other spectral buckets. Frame transfer smear occurs as the additional photons are gained by the added integration time in different spectral locations. The read out time is a very small fraction of the integration time; however, the small error introduced by the frame smear effects is accounted for in the calibration procedures.

These two very distinct factors (out of band and frame transfer smear), cause similar errors on the data stream. While this similarity makes it difficult to distinguish between the two in an attempt to determine which is the source of the error, it allows an estimate of their combined effect to be considered, rather than their individual contributions on the data steam. If measured, translating the measured sensor response to the true response is relatively straight forward. However, directly measuring the function that would be needed to correct these errors is very difficult. These effects can be described via the following equation:

$$tdn_1[1-(p_{12}+p_{13}+\ldots)]+(tdn_2p_{21}+tdn_3p_{31}+\ldots)=mdn_1$$

where: $td_1$ is the true digital number associated with the first spectral position, $mdn_1$ is the measured digital number associated with the first spectral position, and p is the probability that describes the stray and smear light. As Equation (9) illustrates, the measured response of spectral position one is a function of the counts that truly belong in position one but were distributed to neighboring positions, counts that were found in position one but belong to other spectral positions, and counts that both belong and are found in position one.

Using linear algebra, Equation (9) can be expanded and rearranged to incorporate all the sensor's spectral bands and their interactions with their neighbors simultaneously to determine the true digital counts of the data.

$$\overline{mdn}[INV(P)]=\overline{tdn}$$

It should be noted that Equation (10) describes a closed system; there is no possibility for photon gain or loss. Photons that are not registered by the sensor are not considered to exist within this model. For example, digital counts registered by the sensor according to the model belong only to other elements of the CCD and not to a source outside the CCD's bounds. While these limitations are real, Equation (10) utilizes substantially all of the information that is available for a model of the error.

Figure 8C:
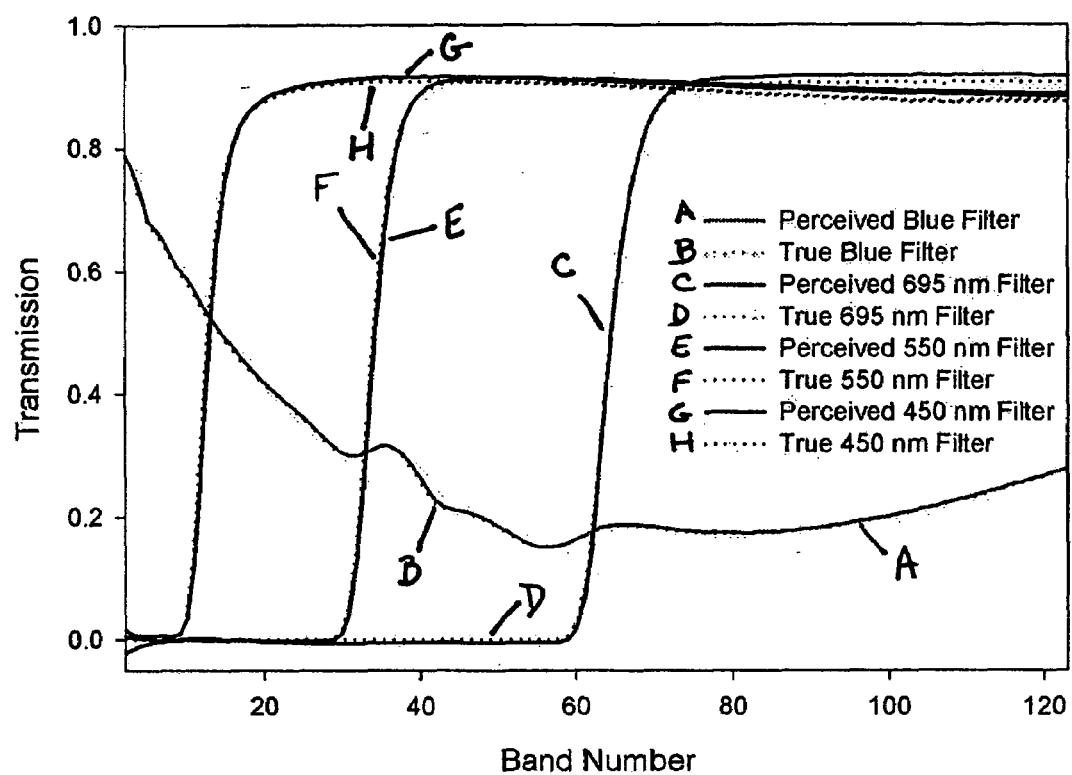
Figure 9:
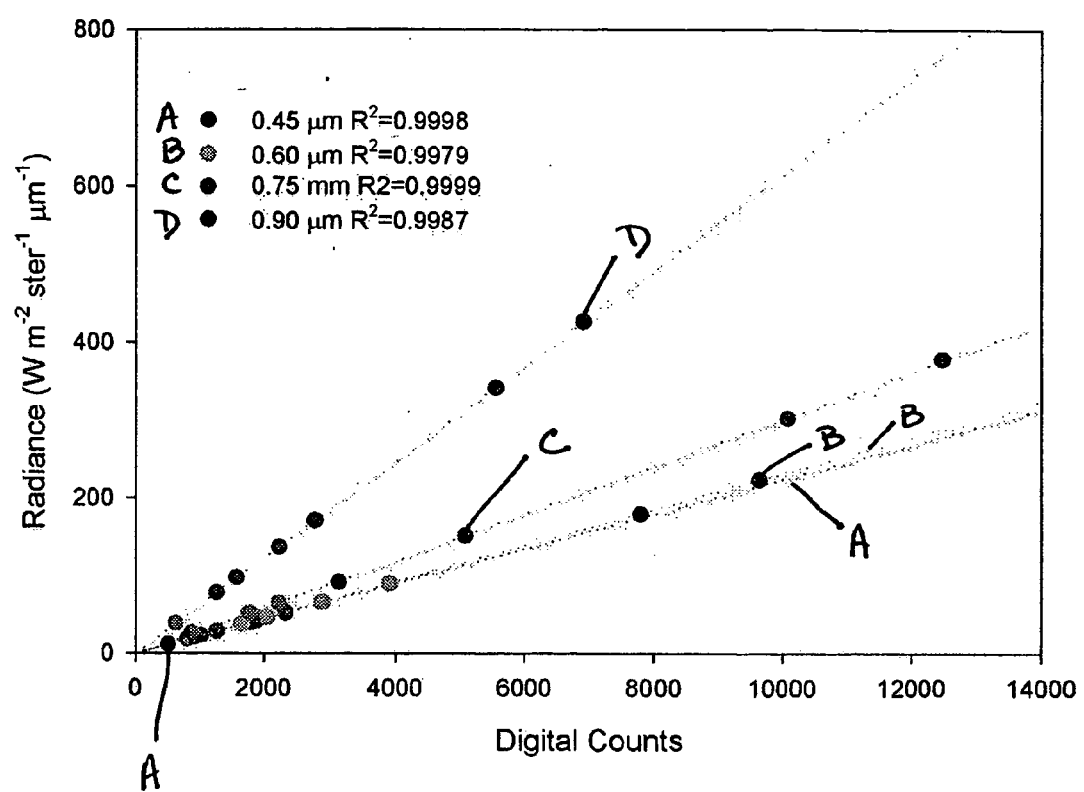
FIG. 9 illustrates that first order regressions adequately describe the relationship between the sensor's response and the physical reality for a variety of spectral and spatial range.

By combining Equations (8) and (10), an optimization may be used to determine a joint flaw probability matrix.

$$\sum_{lamps}\sum_{filters}\sum_{\lambda} abs\left[ \frac{mdn_{filtered}INV(P)}{mdn_{unfiltered}INV(P)} - \overline{tft} \right] \to 0$$

where: tft is the true filter transmission as determined by independent testing. By summing the fitness function over diverse spectral and illumination intensities, the determined probability function approaches the ideal distribution function of the sensor; therefore, this unbiased function is appropriate to employ on a wide range of optical signals. The perceived transmission spectra after the stray light probability correction is applied to the data, as shown in FIG. 8c. The probability matrix is used to correct all of the calibration data and carries through to correct data for elements of interest. for example, using this corrected data for the blue balance filtered and non filtered data over several illumination intensities, a linear regression may be performed to determine the relationship between the observed data and the NIST calibrated source, as shown in FIG. 9. This regression is performed for every element of the CCD to create a radiometric calibration map. This relationship translates the digital counts collected by the camera in the field to the physical units of W $m^{-2}sr^{-1}\mu m^{-1}$.

As illustrated by FIGS. 8a-c, the use of filters in the development of the calibration coefficients dramatically improve spectral imaging.

Figure 10:
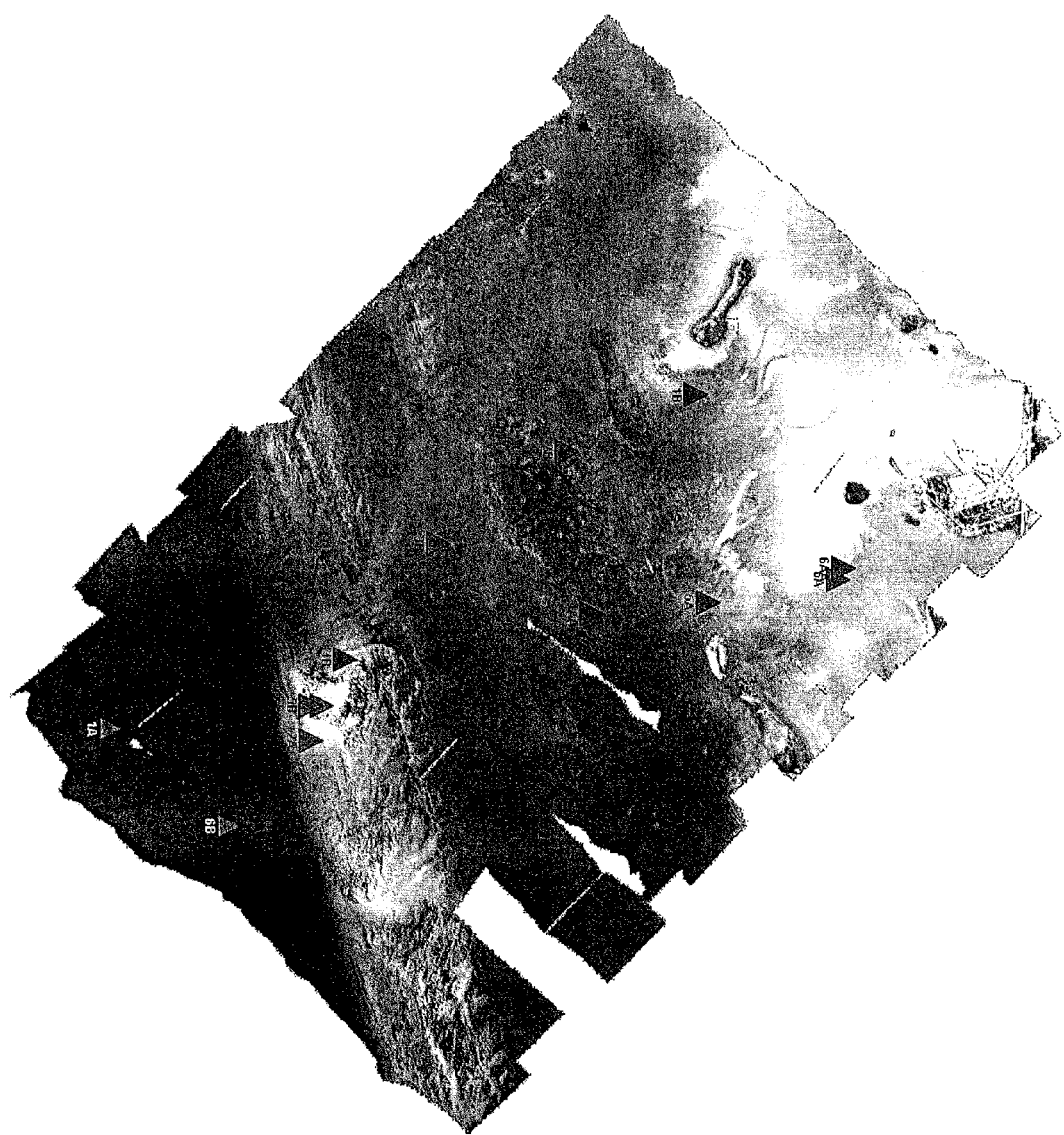
FIG. 10 illustrates an example of a true color RGB (or B and W) image collect by the PHILLS 2 on Oct. 29, 2002 of Looe Key, Fla. The location of the deep and shallow water ground truth stations used in the study are marked as 1A, 1B, 2A, 2B, 3B, 4A, 4B, 4AA, 5A, 5B, 6A, 6B, and 6AA. The drawing is presented as a gray scale of a true color RGB image, as an example.

To compare the improved imaging system with and without sphere filter data, two sets of calibration coefficients were developed. The first set utilized all of the procedures outlined above. The second set used the steps above, except the stray light-frame transfer smear correction was not applied prior to the generation of the radiometric calibration, and only the unfiltered sphere measurements were used in the regression to determine the second set's radiometric calibration. These calibrations were then applied individually to test field data. During this application, the filtered calibration utilized the stray light correction on the field data prior to the calibration's application; the application of the unfiltered calibration did not include this step. In one example, as shown in FIG. 10, images from a flight over Looe Key, Fla. was used to compare filtered and unfiltered calibrations. This data set was selected because of the availability of high quality ground truth data collected coincident to the overflight at the locations shown in FIG. 10. The PHILLS 2 data was collected at an altitude of about 10,000 feet, which yielded about a 2 meter ground spatial resolution.

With both calibrations applied, the effects of the atmosphere were removed so that the results could be compared to the ground truth measurements. Tafkaa, an atmospheric correction program developed by Naval Research Laboratory—DC, was used for this step See, B.-C. Gao, M. J. Montes, Z. Ahmad, and C. O. Davis, "Atmospheric correction algorithm for hyperspectral remote sensing of ocean color from space," Applied Optics 39(6), 887-896 (2000); See, M. J. Monies, B. C. Gao, and C. O. Davis, "A new algorithm for atmospheric correction of hyperspectral remote sensing data," presented at the GeoSpatial Image and Data Exploration II, Orlando, Fla., 2001; and See, B.-C. Gao and C. O. Davis, "Development of a line by line based atmosphere removal algorithm for airborne and spaceborne imaging spectrometers," presented at the Imaging Spectrometry III, 1997. Tafkaa uses look up tables generated with a vector radiative code and includes a correction for sky light reflected off the wind roughened sea surface. The model was run using scene invariant atmospheric parameters that were consistent with the environmental and atmospheric conditions witnessed during the data collect, as shown in Table I.

TABLE I

The atmospheric parameters used in the TAFKAA model runs on the PHILLS It data sets.

| Ozone | 0.247 | Relative Humidity | 98% |
|---|---|---|---|
| Water Column Vapor | 1.985 | Aerosol Model | Tropospheric |
| Tau 550 | 0.05 | Wind Speed | 2 m/s |

Figure 11:
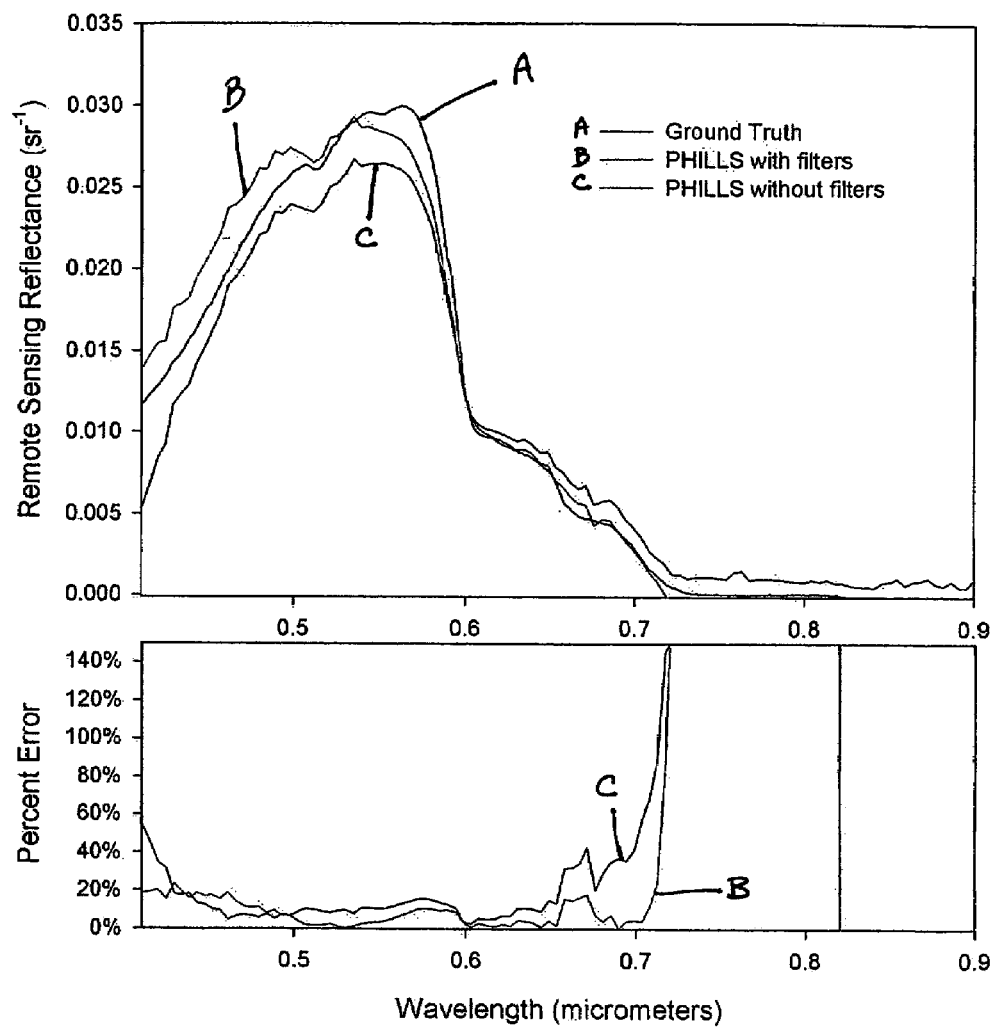
FIG. 11 shows a comparison of the shallow (3.2M) water ground truth remote sensing reflectance and the corresponding results from the PHILLS 2 imagery run through the calibration with and without use of the filters.

With the effects of the atmosphere removed, the data sets were compared to the optical signals measured at the ground truth stations. At the shallow water station (3.2 m), both data sets resembled the ground spectra as shown in FIG. 11. However, the filtered data spectrum had a slightly better fit.

Figure 12:
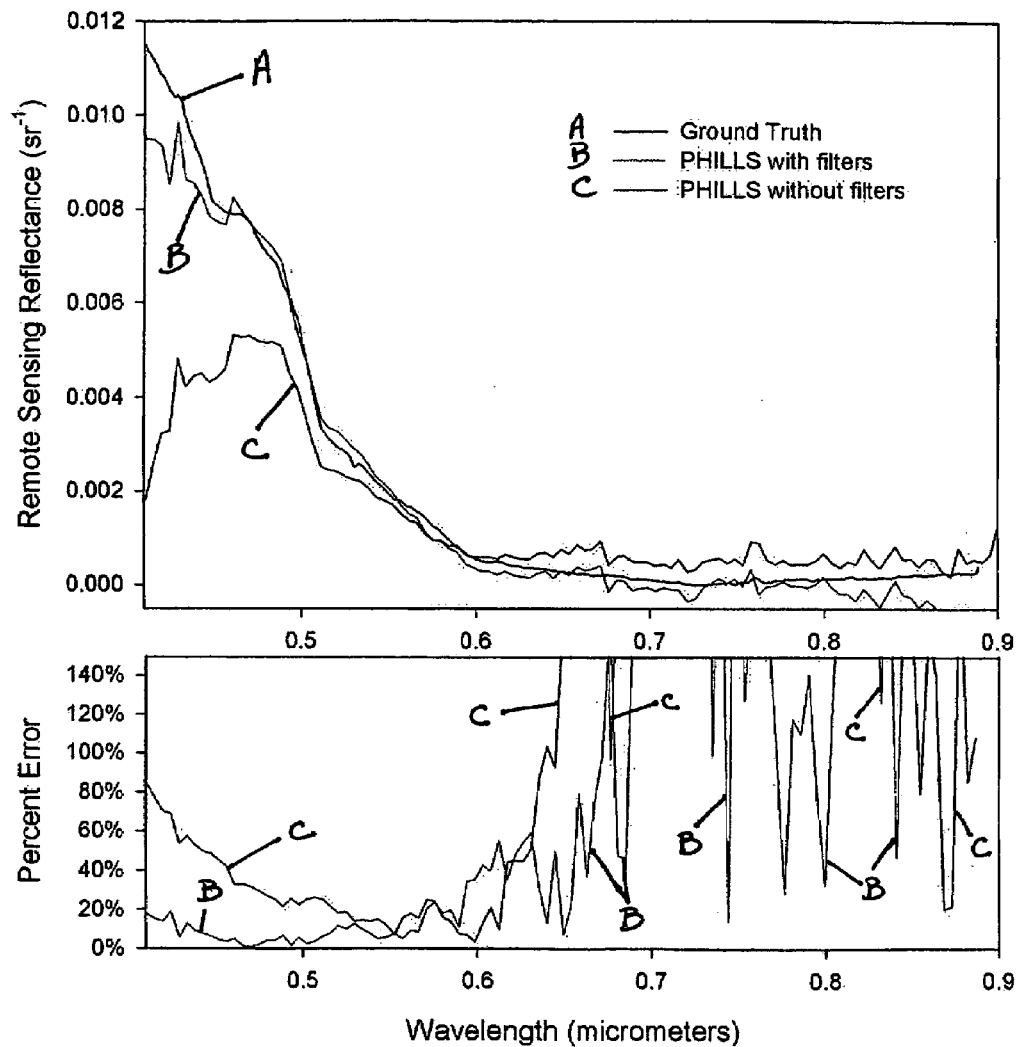
FIG. 12 shows a comparison of the deep (62.5 m) water ground truth remote sensing reflectance and the corresponding results from both the PHILLS 2 imagery run through the calibration with and without filters.
Figure 13:
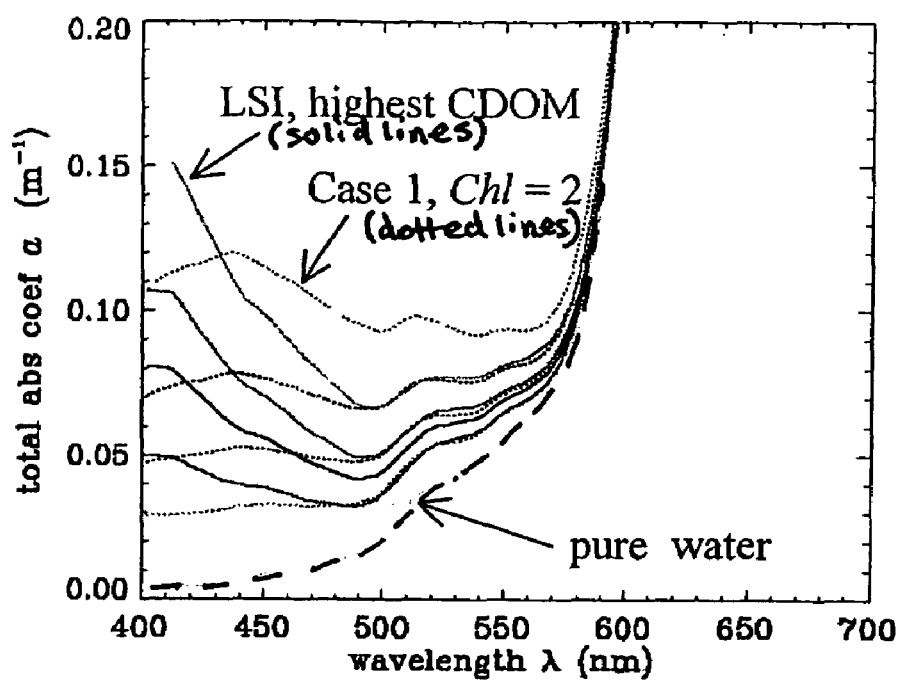
FIG. 13 shows ten total absorption spectra in a LUT database. Solid lines, from LSI ac-9 measurements; dotted lines, from Case 1 bio-optical model for Chl=0.05 to 2 mg m$^{-3}$; dashed line, pure water.
Figure 14:
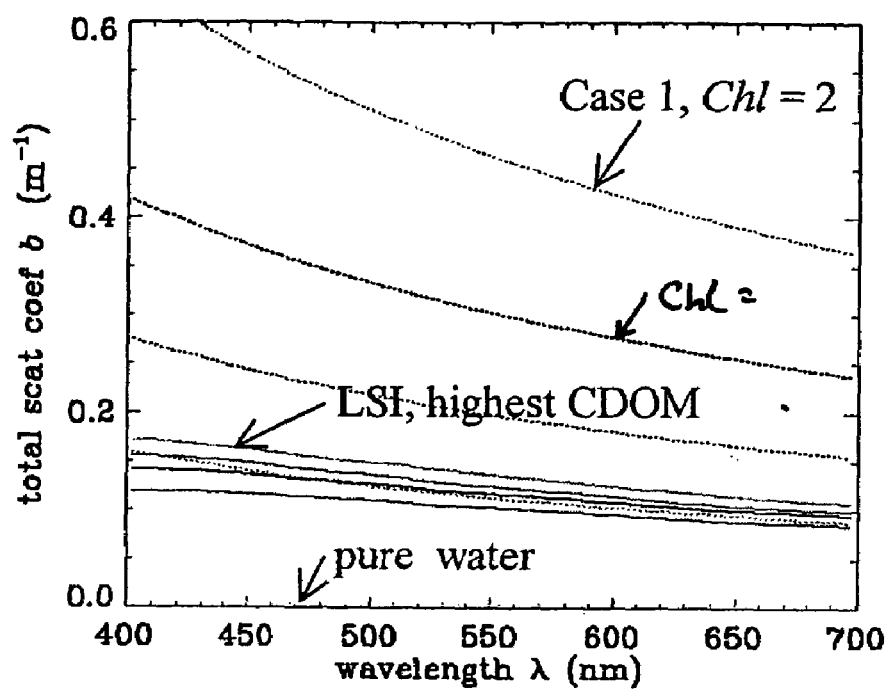
FIG. 14 shows total scattering spectra. Line patterns are the same as in FIG. 1.
Figure 15:
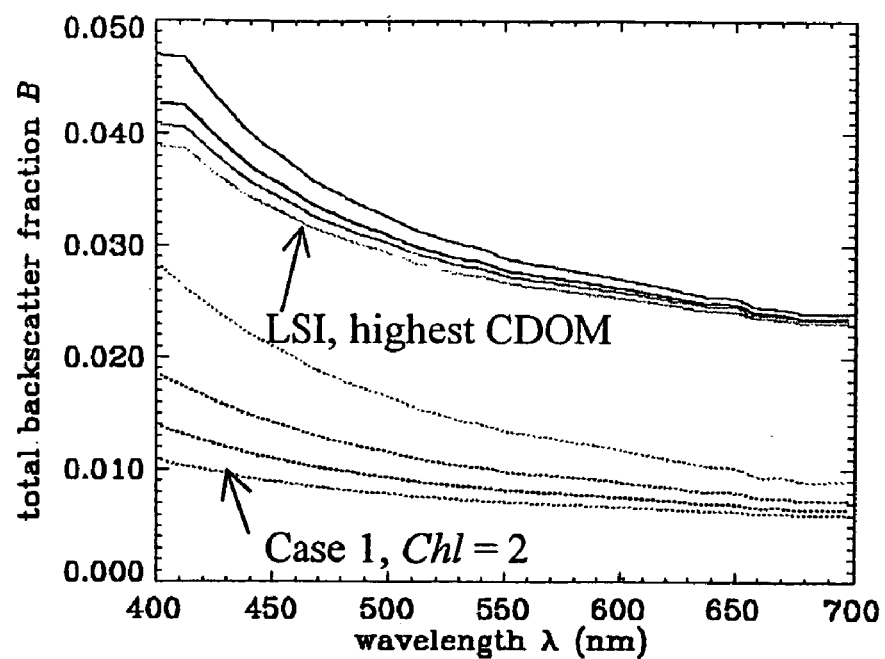
FIG. 15 shows total backscatter fractions. Line patterns are the same as in FIG. 1. The value for pure water is 0.5 at all wavelengths.
Figure 16:
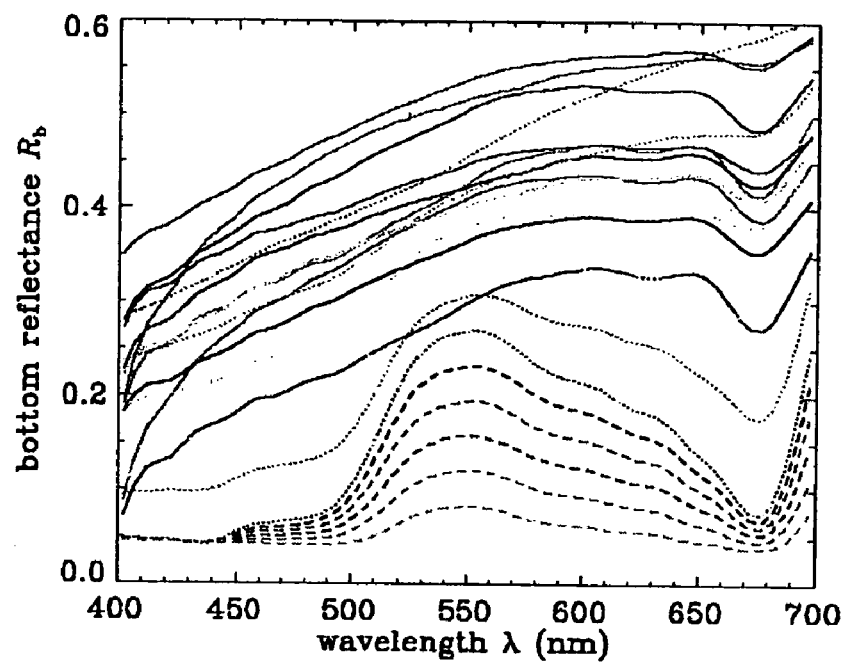
FIG. 16 shows bottom reflectance spectra included in the database.
Figure 17:
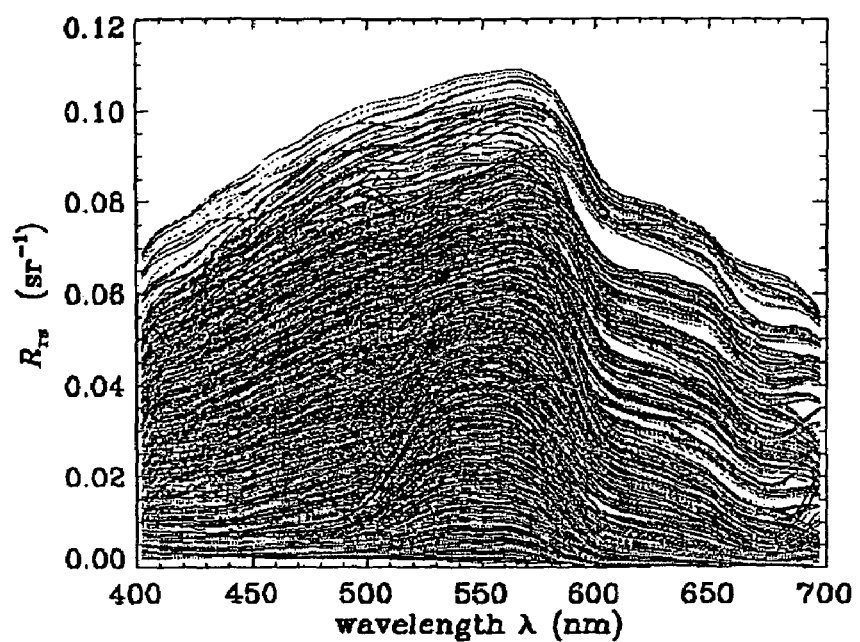
FIG. 17 graphically illustrates the 2,200 $R_{rs}$ spectra in the initial database, showing the broad coverage of possible spectra.
Figure 18:
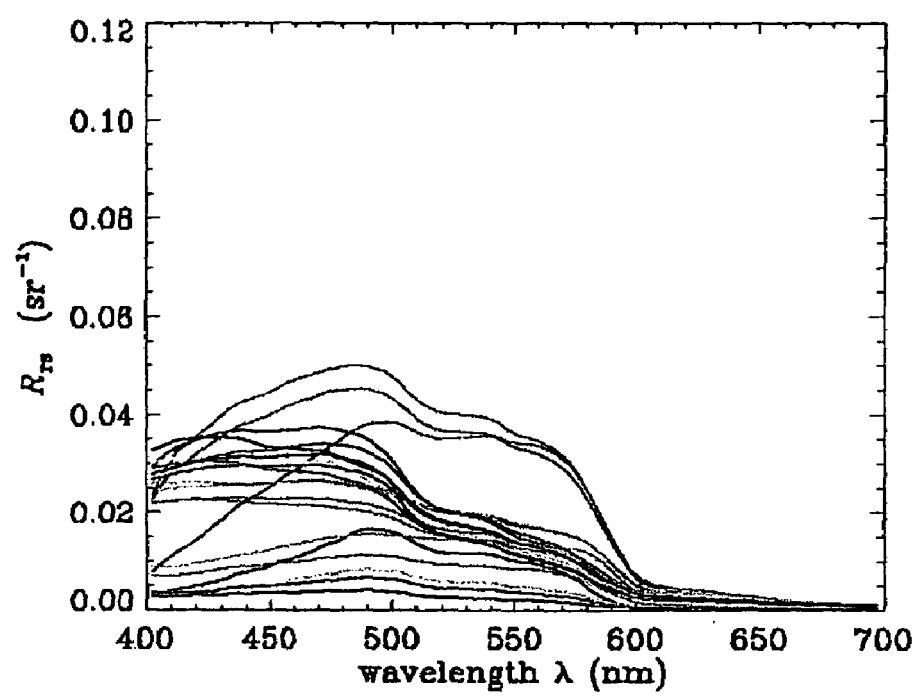
FIG. 18 graphically illustrates the 27 $R_{rs}$ spectra tested.

The minor errors seen in both data sets could be attributed to any combination of unaccounted for sensor noise, flaws in the application of the atmospheric correction, inaccuracies in the geo-registration of the imagery and the ground spectra, or measurement differences between radiometers, for example. The filtered data was clearly superior to the unfiltered data in its comparison to the ground truth spectrum in deeper water (62.5 m) station as shown in FIG. 12. Thus, it is believed that the spectral quality and intensity of the light used during an instrument's calibration improves hyperspectral imaging for coastal and oceanic remote sensing instruments. The emitted signal of the deep water target is so dark that the influences of the stray light and frame smear become increasingly evident. Grating spectrometer based systems typically have on the order of $10^4$ spectral stray light. In addition, an imaging system, such as PHILLS 2, imparts spectral smear during the readout. Other systems may have the same or other second order artifacts, which must be corrected if one is to obtain well calibrated data for frequencies of light that are not well characterized by a standard calibration system used with the instrument.

Look-Up Table Approach

In order to correct for the intervening environment that obscures elements of interest, certain factors that characterize the environment must be determined. In one embodiment, a new technique for extraction of environmental information, such as water inherent optical properties (IOPs) and shallow-water bottom depth ($z_b$) and spectral reflectance ($R_b$) from remotely-sensed hyperspectral ocean-color data, was developed. A look-up-table (LUT) approach compares a measured remote-sensing reflectance ($R_{rs}$) spectrum with tabulated $R_{rs}$ spectra generated by a large number of runs using a radiative transfer numerical model for computing radiance distributions and related quantities, such as the HYDROLIGHT model[1] having a range of water IOPs, bottom depths and reflectances, solar angles and viewing directions. The environmental conditions corresponding to the measured $R_{rs}$ spectrum are assumed to be the same as the input conditions for the run that generated the database $R_{rs}$ spectrum that most closely matches the measured $R_{rs}$ spectrum. Here we show results based on water and bottom conditions at Lee Stocking Island, Bahamas during the Coastal Benthic Optical Properties (CoBOP) field experiments. Non-uniqueness of $R_{rs}$ spectra does not appear to be a problem, and wavelength-uncorrelated random noise does not affect the spectrum matching.

[1]HYDROLIGHT™ is a trademark of SEQUOIA SCIENTIFIC, INC.

LIDAR Systems

Retrieval of the characterization and classification of elements of interest from any fluid, regardless of its density and obscuration are made using knowledge of both the spectral signature of the target and the location of the target within the fluid medium. Use of LIDAR systems offers the capability of ranging the location of the target within the medium, but does not adequately allow for the ability to characterize and classify the target based on the images captured. Also, even a hyperspectral data stream may not be sufficient by itself to range the target as well as resolve the spectral characteristics of the medium and target, simultaneously. By coupling the active LIDAR and passive multi-spectral data streams together, the combined data allows for the complete characterization and classification of the medium and target, simultaneously. The use of such a system compensates for distortions of the intervening environment, such as air, of any type as well as water. The system may also be applied to areas in which draping/aspect are issues, such as mapping leeward mountain forests, the correlation of mineral deposits and seismic faults, vegetation on steep river banks, for example. The system excels in coastal, ocean, estuary, river, and lake areas in which draping/aspect are issues, such as submerged aquatic vegetation mapping, coral reef mapping, the correlation of mineral deposits and seismic faults, and vegetation on steep river banks, for example. Imaging of flowing materials such as lava flows may also benefit from using the system, which corrects for the displacement of the flowing materials.

Spectral reflectance signatures contain a wealth of information about the inherent properties of targets. (See Mobley 1999) A variety of numerical and analytical techniques are available that permit identification and classification of plant types on land and in water, mineralogy, tissue health, etc., that are well known to those skilled in the art of spectral image analysis.

The analysis of spectral reflectance can also be used to characterize the attenuation coefficient for the obscuring media. Application of an accurate attenuation coefficient allows for further improvement of the LIDAR analysis as described below. A three-dimensional spectral data cube may be generated by a conventional spectral sensor containing information about all of the elements of interest within the scene and any fluid media between the sensor and the target, even if the fluid media partially obscures the elements of interest.

Conventional use of LIDAR systems does not allow for detailed characterization of features in a LIDAR image. Several known hyperspectral bathymetric algorithms may be used to determine bottom type, water type, and depth simultaneously. However, a combination of the strengths of multi-spectral, LIDAR and/or bathymetric techniques provides a synergistic recovery of a complete image of the elements of interest with unexpected and surprising detail.

One unique advantage of the present invention is that each sensor system can be expanded to produce improved information in areas overlapping within the information provided by the other complementary systems. This allows for feedback between they systems resulting in much improved classification and characterization of the targets and medium than that produced by any the two systems operating independently. Thus, while LIDAR's ability to classify is limited and multi-spectral imaging's ability to range depths is problematic, a synergistic combination has the ability to generate more information in each of the data gathering areas of the other. By feeding that information simultaneously to a control system, using known feedback algorithms, the elements of interest are characterized with better constraint and refinement.

Referring now to FIG. 1, one embodiment of a combined system 1 also includes an Inertial Navigation System (INS) 2 that couples an Inertial Measurement Unit (IMU) to a Differential Global Positioning System (DGPS) to record the position and viewing geometry of the elements of interest. An additional hyperspectral sensor 3 collects the downwelling and/or upwelling ambient light for correction of the hyperspectral imaging data. Coupled system and platform spatial orientation to the elements of interest are recorded within the Instrument Control Data Acquisition processor 4. In an earth oriented scanning system, global positioning satellites and gravimetric sensors are currently used to determine the viewing geometry. Gyroscopes can be used to stabilize the sensors as the platform orientation changes. In another embodiment, orientation sensors (roll, pitch, and yaw) may be sampled to apply geometric corrections to the sampled data. These systems are well known and all variations are to be considered within the scope of the invention, but are too numerous to detail herein. Methods to stabilize both the target and sensor are well known, and image geometric correction may be unnecessary. Examples are available in the medical arts for delicate procedures requiring stabilization.

In one embodiment, the hyperspectral image detector 5, which is shown in the sensor system of FIG. 1, comprises a pushbroom sensor (not shown) using a high quantum efficiency, two dimensional photon detector such as a back-thinned CCD as described in Mouroulis, et al. 2000. The pushbroom design allows for a more rugged, compact sensor. Spatial information along the cross track dimension is simultaneously integrated in the pushbroom sensor, resulting in a longer integration time and resultant signal to noise level improvements, as shown in FIG. 2. Imaging data 22 from the hyperspectral image detector 5 is fed into the Instrument Control Data Acquisition processor 4 in real time. A diffraction grating 19 causes frequencies of light to be received in the pushbroom sensor 20 in a spectral dimension on the CCD. Thus, a three-dimensional data cube is formed from the hyperspectral image data having two spatial dimensions, which are resolved from the cross track dimension and the position of the airborne platform on the along track dimension, and a spectral dimension as a result of the diffraction of light by the diffraction grating on the surface of the CCD. Each "pixel" 23 contains a spectrum 24, which is resolved into contiguous bands of spectral frequencies having a measured signal intensity versus wavelength, as shown. The spectrum 24 may be used to resolve the particular elements of interest within the spatial area represented by the pixel of data, if the influence of the intervening environment can be determined from the data itself and other sensor measurements.

In another embodiment, a whiskbroom design (not shown) is used whereby an optical scanning method (such as a rotating mirror) is swept across the flight track. The scanning of the whiskbroom design limits the amount of time the detector dwells on each target pixel and introduces a moving optical element that is more difficult to optically quantify by calibration.

The imaging LIDAR 6 (either topographic or bathymetric imaging or both) may use a high frequency, pulsed laser. Any frequency may be used that provides data at a resolution useful to the system For example, topographic LIDAR usually scans at frequencies greater than the 30 kHz range (although LIDAR is not limited to these frequencies), while bathymetric LIDAR scanning frequencies are typically slower, but not necessarily so. LIDAR systems are usually designed with unique source and detector specifications that limit each system to at most a few target types. The specifications and target types are well known and do not need to be listed herein.

In one embodiment, a topographic LIDAR combined with a bathymetric imaging LIDAR images river and shoreline mapping, terrestrial mapping, and wave structure, which allows for improved atmospheric corrections, such as removal of sun glint. The system uses a topographic LIDAR, whose scanning frequencies are at least 30 kHz. The bathymetric imaging LIDAR may use the same scanning frequency or a different scanning frequency. The topographic and bathymetric LIDAR may use different wavelengths, for example, 1065 nm for topography and 532 nm for bathymetry. Other wavelengths and scanning frequencies may be used in alternative embodiments. For example, transmission at two different wavelengths is used to differentially sense targets through the obscuring medium. Any and all wavelengths may be applied, depending on the type of obscuring medium and the types of elements of interest to be sensed in the target locations. Wavelengths can be selected to detect an air-sea interface (e.g., infrared) and the sea bottom or the air-sea interface and elements of interest within the sea (e.g., blue or green), for example.

Also, the time differentials between the two return signals provides a method of determining the depth of the elements of interest and/or total depth of the obscuring medium The differential return of two LIDAR emissions is fundamentally a function of the difference in pathlength between the targets (surface and bottom) and secondarily the attenuation coefficient of the medium, for example. Alternatively, the rithms such as LIDAR depth measurements used to train hyperspectral depth algorithms for faster real-time coverage. Also, spectral imaging data can be used to solve typical bathymetric LIDAR shallow water imaging problems and mine detection problems. The spectral image data records optical properties of the medium, which may be used to improve LIDAR algorithms.

Table 2. Performance of spectrum-matching algorithms SMAI to SMA6 for three noise free test $R_{rs}$ spectra that are similar the LSI-based spectra in the database. IOP=2 means that database IOP spectrum 2 was found to be the best match for the test IOP spectrum, etc. Incorrect retrievals are shown in bold.

|  | test spectrum 1<br>IOP = 0.25(#2) + 0.75(#3)<br>$R_b$ = 0.75(#3) + 0.25(#7),<br>$z_b$ = 4.5 m | test spectrum 2<br>IOP = 0.25(#2) + 0.75(#3)<br>$R_b$ = 0.75(#3) + 0.25(#7),<br>$z_b$ = 12.5 m | test spectrum 3<br>IOP = 0.25(#2) + 0.75(#3)<br>$R_b$ = 0.75(#3) + 0.25(#7),<br>$z_b$ = ∞ |
|---|---|---|---|
| SMA 1: LSQ diff of unnorm $R_{rs}$ (Eq. 1) | IOP = 2; $R_b$ = 3; $z_b$ = 5 m | IOP = 2; $R_b$ = 11; $z_b$ = 10 m | IOP = 3; $R_b$ = 1; $z_b$ = 50 m |
| SMA 2: LSQ diff of length norm (Eq. 3) | IOP = 2; $R_b$ = 3; $z_b$ = 5 m | IOP = 3; $R_b$ = 3; $z_b$ = 15 m | IOP = 3; $R_b$ = 1; $z_b$ = ∞ |
| SMA 3: min angle between length norm (Eq. 4) | IOP = 2; $R_b$ = 3; $z_b$ = 5 m | IOP = 3; $R_b$ = 3; $z_b$ = 15 m | IOP = 3; $R_b$ = 22; $z_b$ = ∞ |
| SMA 4: LSQ of zero offset (Eq. 6) | IOP = 2; $R_b$ = 3; $z_b$ = 5 m | IOP = 2; $R_b$ = 11; $z_b$ = 10 m | IOP = 3; $R_b$ = 1; $z_b$ = 50 m |
| SMA 5: LSQ of zero offset, then length norm | IOP = 2; $R_b$ = 3; $z_b$ = 5 m | IOP = 3; $R_b$ = 3; $z_b$ = 15 m | IOP = 3; $R_b$ = 1; $z_b$ = ∞ |
| SMA 6: LSQ of length norm then zero offset | IOP = 2; $R_b$ = 3; $z_b$ = 5 m | IOP = 3; $R_b$ = 3; $z_b$ = 15 m | IOP = 3; $R_b$ = 1; $z_b$ = ∞ |

LIDAR wavelengths can be tuned to stimulate a variety of fluorescent properties of both elements of interest within an obscuring medium and the obscuring medium, itself, such as chlorophyll, hydrocarbons, coralline and algae growth, Raman, fluorescent dyes, medical properties such as epidermis, carcinoma, and epifluorescence. Imaging data from the imaging LIDAR 6 may be fed into the Instrument Control Data Acquisition processor 4 in real time.

Once the imaging data has been collected by the sensors described above, the information is correlated and processed with the recorded position data in real time in the Instrument Control Data Acquisition processor and may be stored as a three-dimensional spectral data cube. Target and medium classification and characterization data may be determined from this spatially correlated data Examples of this data include use of hyperspectral image data for identification of targets with unique spectroscopic or fluorescence properties, including foliage type (on land) and coral type (in water), for example.

In one embodiment, the Instrument Control Data Acquisition processor 4 is calibrated by known methods to compensate for filters that may be required in certain environments, sensor anomalies due to possible temperature variations and lifetime factors. Other variables may require compensation depending on the target and medium. The processor 4 also monitors field of view and swath comparisons to correlate the data gathered. Algorithms used to classify and characterize the targets and medium may be contained within the processor 4 along with feedback algo- Radiative Transfer Modeling is used to generate a database of remote sensing reflectance [$R_{rs}$] spectra corresponding to various combinations of measured and modeled water-column inherent optical properties [IOPs], bottom reflectance spectra [$R_b$], and bottom depths [$z_b$]. Each $R_{rs}$ spectrum in the database is indexed by labels that identify the IOPs, bottom reflectance Rb, and bottom depth $z_b$ that were used as input to the Radiative Transfer Modeling run that generated the $R_{rs}$ spectrum. Test spectra $R_{rs}$ are generated using other sets of IOPs, $R_b$, and $z_b$ (sometimes similar to those in the database, and sometimes dissimilar). These test spectra are used to evaluate the performance of various possible spectrum-matching algorithms, and spectrum-matching algorithms are chosen that result in improved spectral imaging.

For example, four sets of representative water-column IOPs were measured at Lee Stocking Island, Bahamas and were used in generating a database of $R_{rs}$ spectra for initial evaluation of spectrum matching algorithms. The particle backscatter fraction $B_p = b_{bp}/b_p$ was specified to be 0.02, which may be representative of the mixture of small mineral particles and phytoplankton suspended in the LSI waters, as shown in FIG. 3. The resulting total backscatter coefficients B (including water backscatter, which has $B_{water}$=0.5) then are in the range of 0.025 to 0.05 for LSI waters (see FIG. 3). The total backscatter fraction B at the current wavelength was used to generate the total phase function from the Fournier-Forand family of phase functions as described in Mobley et al. (2002). Both representative and non-representative $R_{rs}$ spectra were added in the database for purposes of evaluating the spectrum matching algorithms for LSI. Six more sets of IOPs were added to the four measured sets for this purpose. The first was simply pure water. The remaining five spectra were generated from the Radiative Transfer Modeling IOP model for Case 1 waters for chlorophyll concentrations of Chl=0.05, 0.20, 0.50, 1.0 and 2.0 mg m$^{-3}$. In these runs, the particle backscatter fraction was set to $B_p$=0.005, which is typical of phytoplankton in Case 1 waters. Although LSI waters typically have Chl concentrations of 0.05 to 0.3 Mg M$^{-3}$, these Case 1 IOPs are not expected to be representative of the waters around LSI, which are Case 2 waters because of the additional CDOM, whose origin is believed to be corals and seagrass. The LSI water also may contain resuspended sediments and small calcite particles that precipitate out of solution. The five total Case I absorption spectra are shown in FIG. 1 as dotted lines. The total scattering coefficients b corresponding to FIG. 1 are shown in FIG. 2. FIG. 3 shows the corresponding total backscatter fraction B.

Twenty-two bottom reflectance spectra were used to generate the bottom reflectance spectrum $R_{rs}$ database: 11 spectra measured on sediments in the vicinity of LSI (shown as solid lines in FIG. 4), fi spectra generated as weighted averages of clean coral sand and green algae (dotted lines in FIG. 4), and 5 spectra that were weighted averages of green algae and a clean seagrass leaf (dashed lines). With the assumption that the bottom BRDF is Lambertian for the incident lighting conditions and viewing geometry, these spectra are equivalent to bottom irradiance reflectance spectra, $R_b=E_u/E_d$.

The bottom depths $R_b$ spectra were applied at nine bottom depth values: $Z_b$=0.5, 1, 2, 5, 10, 15, 20, 30, and 50 m. A tenth option, infinitely deep water, was also included. In this case, the non-Lambertian "bottom" BRDF was computed from the water-column IOPs.

The database in this example thus has 10 sets of IOPs, 22 bottom reflectances, and 10 bottom depths. When combined in Radiative Transfer Modeling runs, these yield 10×22× 10=2,200 $R_{rs}$ spectra. For the initial database, only one solar zenith angle was used: 0,=40 deg, and only the polar cap water-leaving radiances were used to compute $R_{rs}$. Radiative Transfer Modeling runs were made for 60 wavelength bands from 400 to 700 nm; each bandwidth was 5 nm FIG. 5 shows the 2,200 spectra in this initial $R_{rs}$ database.

A small set of $R_{rs}$ spectra were generated to use in developing and evaluating spectrum-matching algorithms. The intention was to have some $R_{rs}$ spectra that corresponded closely to the IOPs, bottom reflectances, and bottom depths used to generate the RS database. These $R_{rs}$, should be easy to match with nearly similar spectra in the database, whose indices would then identify IOPs, reflectances, and depths close to the ones used to generate the test spectra. Other test spectra were generated with IOPs, bottom reflectances, and bottom depths unlike those in the original database. These spectra should, in principle, be hard to match and may lead to recovered IOPs, reflectances, or depths unlike the ones that actually generated the test spectrum There may be $R_{rs}$, spectra in the database that are very similar in shape and magnitude to the test spectra even though they were generated with greatly different IOPs, reflectances, and bottom depths; this is where non-uniqueness may cause problems.

The test spectra had IOPs defined as follows. IOP test spectrum 1 was a weighted average of two of the LSI IOP spectra (25% of LSI ac-9 spectrum 2 and 75% of LSI spectrum 3); these IOPs are thus similar to those used to create the database. IOP test spectrum 2 was generated using the Radiative Transfer Modeling Case 2 water IOP model, with Chl=0.1 Mg M$^{-3}$, $B_P$=0.005; CDOM proportional to Chl as in Case 1 water; and 0.5 gm m$^{-3}$ of calcareous sand with $B_P$=0.03. IOP test spectrum 3 was similar to spectrum 2, except that the mineral component was 1 gm m$^{-3}$ of red clay particles with $B_P$=0.02. IOP spectra 2 and 3 are quite different from any of those in the database.

Figure 6:
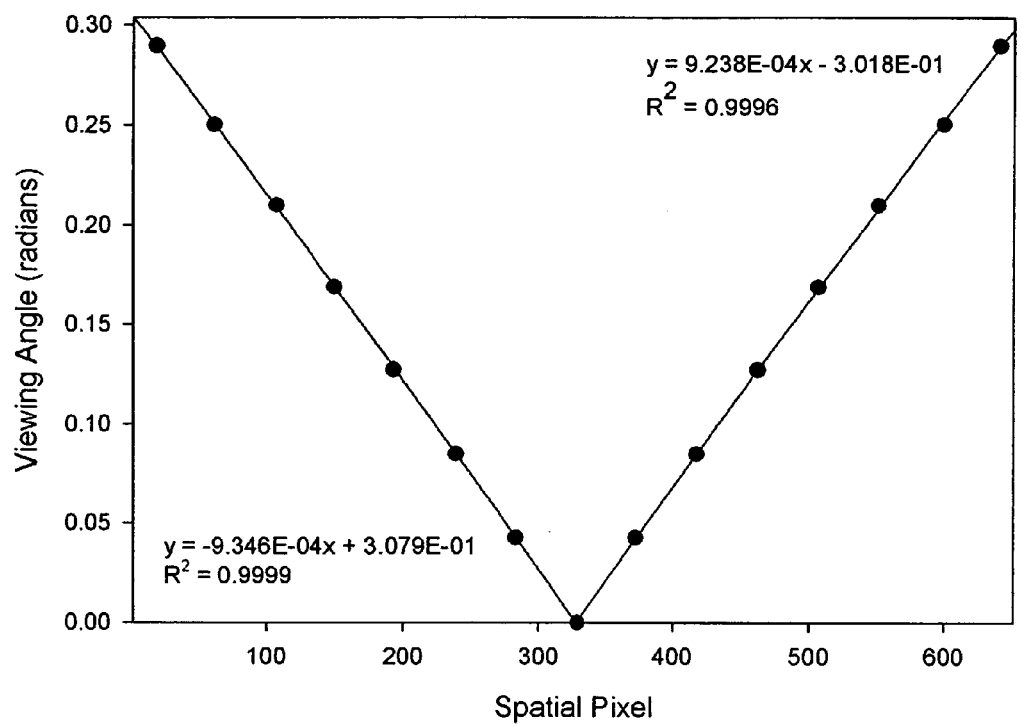
FIG. 6 shows a graph of two first order regressions describing the relationship between the viewing angle and observed PHILLS 2 spatial pixel at spectral pixel 35 (557 m).
Figure 7:
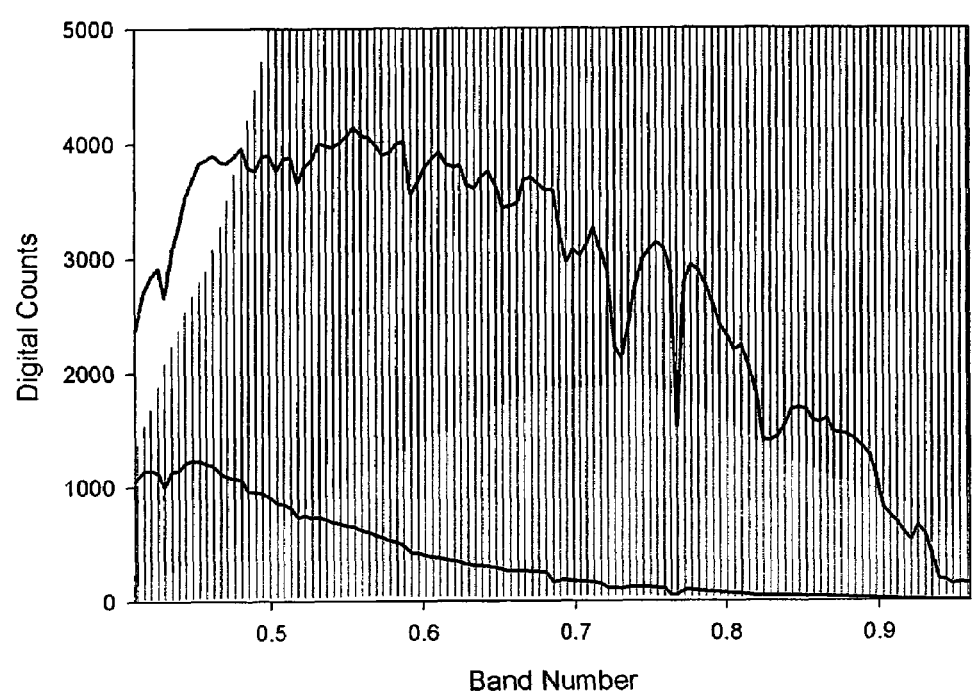
FIG. 7 shows observed dark corrected sand and deep water spectra overlaid on the radiometric bounds of the integrating sphere with (blue and green) and without (blue only) the use of filters for a PHILLS 2 sensor.

Three test bottom reflectance spectra were defined as follows. $R_b$ test spectrum 1 was a weighted average of two LSI spectra (25% of LSI spectrum 7 and 75% of LSI spectrum 3, both of which are sand spectra). Rb test spectrum 2 was a weighted average of 25% coral sand and 75% red algae. Rb test spectrum 3 represents gray mud and has a reflectance of 0.1 at all wavelengths. Again, $R_b$ spectrum 1 is similar to spectra in the database, and spectra 2 and 3 are unlike any spectra in the database. Three bottom depths were used: $z_b$=4.5 m (close to the database value of 5 m), 12.5 m (half way between database values of 10 and 15 m), and infinite. The test IOP, $R_b$, and $z_b$ data were then used to generate 3×3×3=27 $R_{DS}$ test spectra, which are shown in FIG. 6.

There are many criteria that can be used to match a given spectrum $R_{rs}$. with one in the $R_{rs}$ database. Let $R_{rs}(i,\lambda_j)$ denote the it spectrum in the database, i=I to I (I=2200 at present), which is defined for discrete wavelengths $\lambda_j$, j=1 to J(J=60 at present). Let w(j) be a weighting function that can be chosen to de-emphasize wavelengths where the data are of suspicious quality or carry less information. The weighting function satisfies $0 \leq w(j) \leq 1$ for each j. Setting w(j)=1 for each j gives each wavelength equal importance. Setting w(j)=0 for a particular j omits that wavelength from use in the matching algorithm A few simple candidate spectrum-matching algorithms (SMAs) are then defined as follows.

SMA1: Least-squares matching of the absolute spectra: The database spectrum that most closely matches the given spectrum $R_{rs}$ is the one that minimizes $$LSQabs(i) = \sum_j \left\{ w(j)\left[R_{rs}(i, \lambda_j) - \tilde{R}_{rs}(\lambda_j)\right]^2 \right\}.$$

The value of i giving the minimum value of LSQabs(i), call it $i_{min}$ is just the record index of the database system.

SMA2: Least-squares matching of length-normalized spectra. If the spectra are relative values (such as digital counts) or may have multiplicative errors, then it makes sense to normalize each spectrum by its euclidian length in J-dimensional wavelength space, defined as $$|R_{rs}(i)| = \sqrt{\sum_j R_{rs}^2(i, \lambda_j)}.$$

The quantity to be minimized is then $$LSQnorm(i) = \sum_j \left\{ w(j)\left[\frac{R_{rs}(i, \lambda_j)}{|R_{rs}(i)|} - \frac{\tilde{R}_{rs}(\lambda_j)}{|\tilde{R}_{rs}|}\right]^2 \right\}.$$

Algorithm (3) will regard two spectra as being the same if they differ only by a multiplicative factor.

SMA3: Angle-matching of length-normalized spectra. Using the same normalization as in algorithm (3) to covert the spectra to unit vectors, the cosine of the "angle" between the unit vectors is then $$\cos(\theta_i) = \sum_j \left\{ w(j) \frac{R_{rs}(i, \lambda_j)}{|R_{rs}(i)|} \frac{\tilde{R}_{rs}(\lambda_j)}{|\tilde{R}_{rs}|} \right\}.$$

The closest spectrum in the database is the one that maximizes $\cos(\Theta_i)$, i.e., that minimizes the angle between the two unit vector spectra. Two spectra that differ only by a multiplicative factor will have a cosine of 1, i.e., an angle of 0 between them. If w(j)=1 for all j, algorithm (4) corresponds to the matching criterion used in the Spectral Image Processing System (SIPS; see Kruse, et al., 1993).

SMA4: Least-squares matching of offset spectra. If the spectra may have additive errors (such as from imperfect removal of a wavelength-independent dark current value), then it makes sense to shift the spectra to a common baseline value. For example, each spectrum can be shifted so that its minimum value is zero. Let $$\min R_{rs}(i) = \min_j R_{rs}(i, \lambda_j)$$

Then the spectra are compared using $$LSQoffset(i) = \sum_j \left\{ w(j) \left[ (R_{rs}(i, \lambda_j) - \min R_{rs}(i)) - (\tilde{R}_{rs}(\lambda_j) - \min \tilde{R}_{rs}) \right]^2 \right\}.$$

SMA5: Least-squares matching of zero-offset, then length-normalized spectra. The additive and multiplicative normalizations can be combined. One can first shift the spectra to a common baseline value of zero, as in 5.4, and then normalize to unit length as in 5.2. The least-squares fit of the resulting shifted, normalized spectra is then used to find the closest match.

SMA6: Least-squares matching of length-normalized, then zero-offset spectra. Alternatively, one can first normalize the spectra to unit length and then shift them to zero at their minimum value. The least-squares fit of the resulting normalized, shifted spectra is then used to find the closest match. Note that zero-shifting and unit-normalization are not commutative; thus algorithms 5.5 and 5.6 are in principle different.

There are other possible spectrum-matching algorithms, such as matching wavelength derivatives.

Table 2 shows the results for three test $R_{rs}$ spectra that are based on LSI Iop and $R_b$ spectra, and which have $z_b$ values close to those in the database. Recall that test Iop spectrum 1 (which is used here) is a weighted average of two of the LSI Iop spectra (25% of LSI ac-9 spectrum 2 and 75%, of LSI spectrum 3). Test $R_b$ spectrum 1 (used here) is a weighted average of two LSI sediment spectra (25% of LSI spectrum 7 and 75% of LSI spectrum 3, both of which are sand spectra). The three bottom test depths were 4.5 m (near the database value of 5 m)., 12.5 m (in between 10 and 15 m in the database), and infinitely deep. In retrieving the Iops, bottom reflectance, and depth for these test spectra, we should be overjoyed if the spectrum-matching algorithm concludes that the Iops were either database Iop spectrum 2 or 3, database $R_b$ spectrum 3 or 7, and depth 5 m (for test spectrum 1, which has $z_b$=4.5 m), 10 or 15 m (for test spectrum 2, which has $z_b$=12.5 rn), or infinitely deep. As seen in Table 1, each spectrum-matching algorithm concluded that the water Iops were database spectrum 2, $R_b$ spectrum 3, and bottom depth $z_b$=5 m. The retrieval of environmental information is thus considered to be correct in all cases.

Test spectrum 2 was a bit harder because the bottom was deeper, making it harder to distinguish bottom reflectance effects in the $R_{rs}$ spectrum. Nevertheless, four of the matching algorithms concluded that the Iops were database spectrum 3, $R_b$ spectrum 3, and bottom depth 15 m, which are all acceptable. Two of the matching algorithms gave Iop spectrum 2, and bottom depth 10 m, which are acceptable, but chose bottom reflectance spectrum 11. However, database Rb spectrum 11 is another sand spectrum, so this probably also should be regarded as an acceptable recovery.

Test spectrum 3 had infinitely deep water. Each matching algorithm gave IOP spectrum 3, which is acceptable. Each of the algorithms placed the bottom depth at either 50 m or infinite, either of which could be considered acceptable because 50 m is very deep water and not much different from infinite as regards the bottom effect on $R_{rs}$. Five of the algorithms gave bottom reflectance spectrum 1, presumably because no spectrum was ever better than the first one considered, since the bottom was infinitely deep and no bottom spectrum from the tabulated values was used in the Radiative Transfer Modeling runs to generate these $R_{rs}$, spectra.

Thus all of the spectrum-matching algorithms performed acceptably well, i.e. they recovered environmental data from the database that was close to what was used to generate the test spectra Of course, these test cases were rather ideal. In particular, there was no noise in the database or test $R_{rs}$ spectra. However, the addition of even large amounts of wavelength-uncorrelated random noise seldom changed the retrieval. This is because in comparing the spectra over the 60 wavelengths, e.g., via Eq. (1), we are essentially summing 60 zero-mean random deviates, which nearly sum to zero.

The test set also contained 24 $R_{rs}$ spectra that were purposely constructed with IOPs and bottom reflectances that were not representative of the IOP and Rb spectra used to construct the database. These 24 spectra had either IOPs, or $R_b$ spectra, or both, that did not correspond to any IOP and $R_b$ spectra in the database. Nevertheless, the bottom depth was often accurately retrieved when the water was shallow. There were 48 recoveries of bottom depth for which the test spectrum had zb=4.5 m (8 spectra times 6 algorithms). In 35 of the 48 retrievals (78%), the bottom depth was correctly retrieved to be 5 m (the closest depth in the database). In 9 of 48 retrievals the 4.5 m bottom depth was recovered as 10 m, and in 4 cases as 15 m For the 48 recoveries where the true bottom depth was 12.5 m, the recovered depth was 10 m (10 times), 15 m (11 times), 20 m (21 times), and 30 m (6 times). Thus 44% of the: depth recoveries could be regarded as correct in the sense that the closest database values were chosen.

Wavelength-uncorrelated random noise does not greatly impede the spectrum matching. The choice of spectrum-matching algorithm is not critical, and wave length-uncorrelated random noise is not likely to be a problem.

In another example, the LUT approach was applied merely to signals from a passive hyperspectral imaging sensor, without the use of an active LIDAR. This approach allows uncomplicated operation of the system on a satellite, for example, where power constraints and distance make use of an active LIDAR more difficult and expensive. The results showed excellent results for returning accurate bathymetry, using only the passive hyperspectral imaging sensor on an airborne platform at about 10,000 feet. The system is particularly useful for applications where access to the marine environment is denied, even if an incomplete database of IOPs and bottom type is used.

Figure 19:
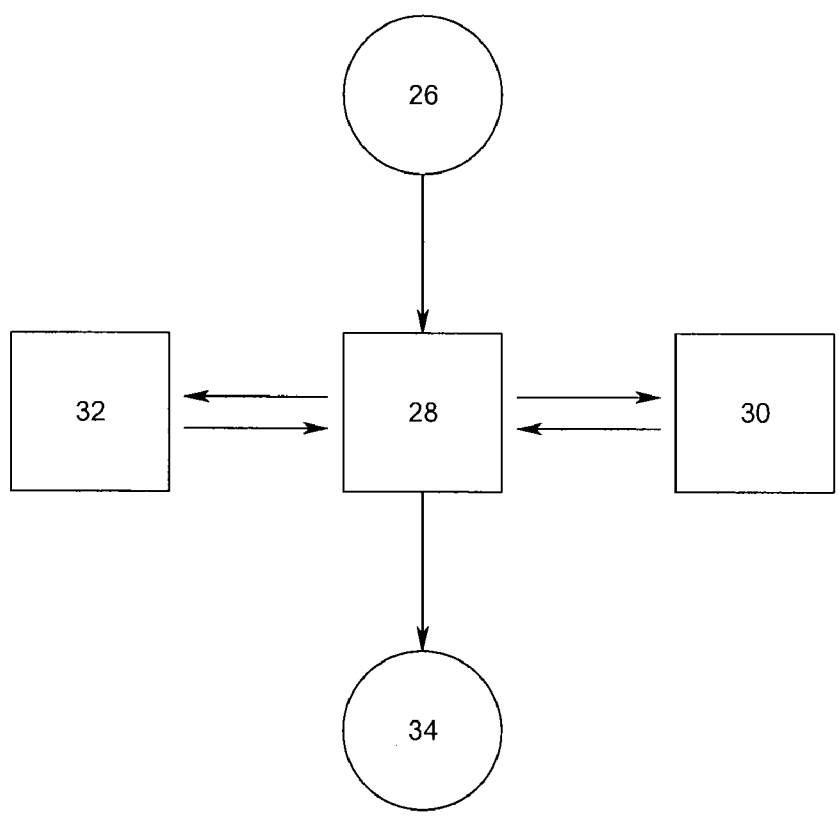
FIG. 19 schematically depicts a flow chart for a process according to one example.

In FIG. 19, a flow chart for a process used in a system for correcting siguals from a passive sensor is shown. As shown in the flow chart, the system includes a look up table 30 of known, tabulated, remote-sensing reflectance spectra. A processing system 28 is capable of accessing the look up table 30 and comparing the known, tabulated remote-sensing reflectance spectra with actual, remote-sensing reflectance signals received from the passive spectral imaging sensor. An algorithm 32 selects an appropriate, known, tabulated remote-sensing reflectance spectra that is comparable to the actual remote-sensing reflectance spectra. Environmental information associated with the known, tabulated remote-sensing spectra are applied, such that the system for correcting signals from the passive spectral imaging sensor is capable of operatively removing from the signals at least a portion of undesirable artifacts caused by an intervening, obscuring environment, yielding the corrected signals 34.

Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. A spectral imaging system for imaging elements of interest in an intervening, obscuring environment, the system comprising:
    a passive spectral imaging sensor;
    an active detection and ranging sensor, capable of emitting pulses of electromagnetic radiation having a narrow band of frequencies and sensing the return of the pulses;
    at least one airborne platform;
    at least one position and attitude detection system; and an instrument control and data acquisition system, wherein the at least one position and attitude detection system, the passive spectral imaging sensor and the active detection and ranging sensor are mounted on the at least one airborne platform and signals from the at least one position and attitude detection system, the passive spectral imaging sensor and the active detection and ranging sensor are operatively received by the instrument control and data acquisition system, such that the signals are stored as a three-dimensional data cube recording two spatial dimensions and a spectral dimension.

2. The spectral imaging system of claim 1, wherein the passive spectral imaging system comprises a pushbroom sensor.

3. The spectral imaging system of claim 2, wherein the pushbroom sensor comprises a backthinned charged couple device.

4. The spectral imaging system of claim 2, wherein the pushbroom sensor comprises a diffraction grating, such that electromagnetic radiation having a range of frequency and entering the sensor is diffracted and the angle of diffraction depends on the frequency, wherein the electromagnetic radiation is spread across the backthinned charged couple device, providing a spectral dimension to the signals generated by the backthinned charged couple device.

5. The spectral imaging system of claim 4, wherein the passive spectral imaging sensor shielded from at least a portion of stray, undiffracted light.

6. The spectral imaging system of claim 5, wherein the passive spectral imaging sensor is calibrated using a multi-step process that includes spectral calibration and radiometric calibration, such that a calibration map is derived that is applied by the instrument control and data acquisition system to the signals received from the passive spectral imaging sensor, accounting for all viewing angles of the passive spectral imaging sensor.

7. The spectral imaging system of claim 6, wherein the calibration map further accounts for the combined residual stray light and frame transfer smear in the signals received by the instrument control and data acquisition system from the passive spectral imaging sensor.

8. The spectral imaging system of claim 1, further comprising: a system for correcting signals from a passive sensor for the environment, the system for correcting signals comprising:
    a look up table of known, tabulated remote-sensing reflectance spectra;
    a processing system that is capable of accessing the look up table and comparing the known, tabulated remote-sensing reflectance spectra with actual remote-sensing reflectance signals received from the passive sensor; and
    an algorithm that selects an appropriate known, tabulated remote-sensing reflectance spectra that is comparable to the actual, measured remote-sensing reflectance spectra, such that environmental information associated with the known, tabulated remote-sensing reflectance spectra are applied for correcting the signals from the passive sensor for the environment; wherein the system for correcting signals from a passive sensor is operatively coupled to the passive spectral imaging system and the instrument control and data acquisition system, such that data recorded in a three-dimensional data cube is corrected to remove undesirable artifacts in the signals caused by the environment.

9. The spectral imaging system of claim 1, wherein the at least one airborne platform comprises a plurality of platforms, each having at least one position and attitude detection system, such that the instrument control and data acquisition system operatively integrates the signals from each of the plurality of platforms, such that the signals are stored as a three-dimensional data cube recording two spatial dimensions and a spectral dimension.

10. The spectral imaging system of claim 1, wherein the at least one airborne platform is a single satellite.

11. The spectral imaging system of claim 1, wherein the at least one airborne platform is a single aircraft.

12. The spectral imaging system of claim 11, wherein the aircraft is lighter than air at sea level.

13. The spectral imaging system of claim 1, wherein the at least one position and attitude detection system comprises at least one gyroscope.

14. The spectral imaging system of claim 13, wherein the at least one position and attitude detection system further comprises a differential global positioning satellite receiver.

15. The spectral imaging system of claim 13, wherein the at least one position and attitude detection system is capable of determining the yaw, pitch and roll of the airborne platform.

16. A spectral imaging system for imaging elements of interest in an intervening, obscuring environment, the system comprising:

a passive spectral imaging sensor;

a system for correcting signals from the passive spectral imaging sensor the system comprising a look up table of known, tabulated remote-sensing reflectance spectra; a processing system that is capable of accessing the look up table and comparing the known, tabulated remote-sensing reflectance spectra with actual remote-sensing reflectance signals received from the passive spectral imaging sensor; and an algorithm that selects an appropriate known, tabulated remote-sensing reflectance spectra that is comparable to the actual, measured remote-sensing reflectance spectra, wherein environmental information associated with the known, tabulated remote-sensing reflectance spectra are applied, such that the system for correcting signals from the passive spectral imaging sensor is capable of operatively removing from the signals at least a portion of undesirable artifacts caused by an intervening, obscuring environment;

at least one airborne platform; at least one position and attitude detection system; and an instrument control and data acquisition system, wherein the at least one position and attitude detection system and the passive spectral imaging sensor are mounted on the at least one airborne platform and signals from the at least one position and attitude detection system and the passive spectral imaging sensor are operatively received by the instrument control and data acquisition system and the system for correcting signals from a passive sensor for correcting the signals, such that the signals are stored as data, the data being corrected to remove undesirable artifacts in the signals caused by the environment and being stored in a three-dimensional data cube, recording two spatial dimensions and a spectral dimension.

17. The spectral image system of claim 16, wherein the environmental information is selected from the group consisting of water inherent optical properties, shallow- water bottom depth, solar angles, viewing directions, and spectral reflectance.

18. The spectral image system of claim 16, wherein at least a portion of the look up table of known, tabulated remote-sensing reflectance spectra is generated using a radiative transfer numerical model for computing radiance distributions and related quantities, having a range of water inherent optical properties, bottom depths, bottom reflectances, solar angles, and viewing directions that are substantially similar to the range of water inherent optical properties, bottom depths, bottom reflectances, solar angles and viewing directions expected for elements of interest that are to be imaged by the passive sensor.

19. A method of calibration of a passive spectral imaging system, comprising:

conducting a spectral calibration of the passive spectral imaging system;

conducting a radiometric calibration of the passive spectral imaging system;

deriving, from the preceding steps of conducting, a correction factor; and applying the correction factor to an instrument control and data acquisition system that receives signals from the passive spectral imaging system, accounting for diffraction of electromagnetic radiation from all viewing angles of the passive spectral imaging sensor.

20. The method of claim 19, wherein the step of conducting a spectral calibration comprises:
    (a) placing a first spectral element lamp in front of a sensor in the passive spectral imaging system;
    (b) positioning, between the lamp and the sensor, a piece of ground glass, such that the entire aperture of a detector is illuminated by the spectral element lamp;
    (c) collecting data from the sensor;
    (d) replacing the first spectral element lamp with another spectral element lamp having a different range of emission frequencies;
    (e) repeating steps (d) and (c) until data is collected for a full spectral range of the sensor; and
    (f) calculating a regression of the known spectral wavelengths that correlates with the position of the pixels within the sensor in which a response was recorded.

21. The method of claim 20, wherein the step of conducting a spectral calibration further comprises fitting a Gaussian curve to the element lamp data for each element lamp used in the calibration and equating the position of the peak of the Gaussian curve to a true spectral position within the sensor.

22. The method of claim 21, wherein the step of conducting a spectral calibration further comprises generating a smile-tilt map of the sensor and using the smile-tilt map to warp all future signals produced by the sensor to a set wavelength vector, during both subsequent calibration steps and normal data collection.

23. The method of claim 19, further comprising a step of conducting an angular response characterization.

24. The method of claim 23, wherein the step of conducting an angular response characterization comprises generating a keystone for the sensor.

25. The method of claim 24, wherein the step of generating a keystone for the sensor comprises:

positioning a physically thin spectral light source a distance from the sensor, such that light source illuminates only one pixel width;

positioning the light source at the distance and inline with the center of the sensor's focal plane;

repeatedly repositioning the light source at predetermined intervals, while keeping the light source in a plane perpendicular to the line between the sensor and the light source;

recording the response from the sensor before and during the step of repeatedly repositioning;

deriving the apparent angular displacement of the source, as determined from a regression against an actual measured relative position between the sensor and the light source.

26. The method of claim 19, wherein the step of conducting a radiometric calibration comprises:

selecting a known radiometric calibration standard having a spectra; employing a series of filters selected to correct the spectra, such that the spectra is substantially representative of the spectra encountered during normal use of the sensor;

adjusting lamp intensities to provide a calibration series that substantially covers the spectral range of elements of interest during normal use;

calculating a stray light probability correction;

determining a radiometric calibration map; and applying the radiometric calibration map to all of the signals generated by the sensor.

27. The method of claim 26, wherein the radiometric calibration standard is a ten lamp, 40-inch diameter, integrating sphere, utilizing tungsten-halogen lamps that are calibrated to known NIST-traceable standards, and the series of filters are three long-pass cutoff filters and three blue balancing filters.

28. The spectral imaging system of claim 8, wherein the passive spectral imaging sensor is shielded from at least a portion of stray, undiffracted light, and the passive spectral imaging sensor is calibrated using a multi-step process that includes spectral calibration and radiometric calibration, such that a calibration map is derived that is applied by the instrument control and data acquisition system to the signals received from the passive spectral imaging sensor, accounting for all viewing angles of the passive spectral imaging sensor and the combined residual stray light and frame transfer smear.

* * * * *